US006444833B1

United States Patent
Ewen et al.

(10) Patent No.: US 6,444,833 B1
(45) Date of Patent: Sep. 3, 2002

(54) METALLOCENE COMPOUNDS, PROCESS FOR THEIR PREPARATION AND THEIR USE IN CATALYTIC SYSTEMS FOR THE POLYMERIZATION OF OLEFINS

(75) Inventors: John A. Ewen, Houston, TX (US); Michael J. Elder; Robert L. Jones, both of Elkton, MD (US)

(73) Assignee: Basell Technology Company BV, Hoofddorp (NL)

( * ) Notice: Subject to any disclaimer, the term of this patent is extended or adjusted under 35 U.S.C. 154(b) by 0 days.

(21) Appl. No.: 09/461,858

(22) Filed: Dec. 15, 1999

(51) Int. Cl.[7] .......................... C07F 17/00; C07F 7/00; B01J 31/00; C08F 4/44

(52) U.S. Cl. .......................... 556/11; 556/12; 556/21; 556/28; 556/30; 556/43; 556/53; 556/58; 556/70; 556/87; 556/406; 534/11; 534/15; 549/3; 549/32; 502/103; 502/117; 526/160; 526/943

(58) Field of Search .......................... 556/11, 12, 28, 556/21, 30, 43, 53, 70, 87, 406, 58; 534/11, 15; 549/3, 32; 502/103, 117; 526/160, 943

(56) References Cited

U.S. PATENT DOCUMENTS 5,489,659 A  2/1996  Sugano et al. ............... 526/127

FOREIGN PATENT DOCUMENTS

| EP | 129 368 A1 | 12/1984 |
| WO | WO 98/22486 | 5/1998 |
| WO | WO 99/21899 | 5/1999 |

OTHER PUBLICATIONS

Knight, "Alkylations of Vinyl Carbanions," in *Comprehensive Organic Synthesis*, Eds. B. Trost, et al. Pergamon Press: Oxford, vol. 3, Part 1.6, p. 241 (1991).

Primary Examiner—Porfirio Nazario-Gonzalez
(74) Attorney, Agent, or Firm—Bryan Cave LLP

(57) ABSTRACT

A class of metallocene compounds is disclosed having the general formula (I):

$$\text{(I)}$$

Figure 1:
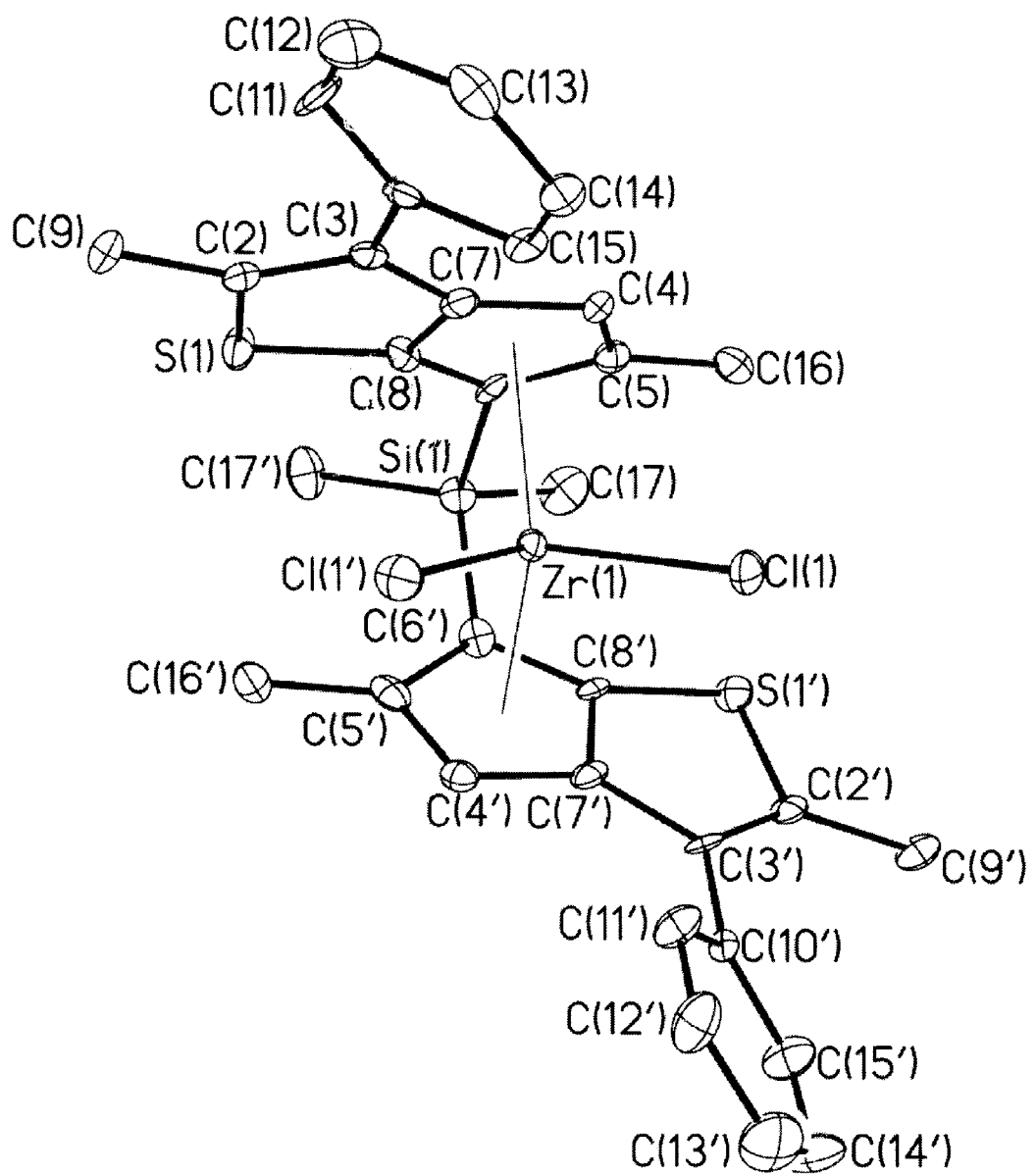

wherein Y is a moiety of formula (II)

$$\text{(II)}$$

wherein A, B and D, same or different from each other, are selected from an element of the groups 14 to 16 of the Periodic Table of the Elements (new IUPAC version), with the exclusion of nitrogen and oxygen; $R^1$, $R^2$, $R^3$, $R^4$ and $R^5$ are hydrogen or hydrocarbon groups, Z is selected from a moiety of formula (II) as described above and from a moiety of formula (III):

$$\text{(III)}$$

wherein $R^6$, $R^7$, $R^8$ and $R^9$, are hydrogen or hydrocarbon groups; L is a divalent bridging group; M is an atom of a transition metal selected from those belonging to group 3, 4, 5, 6 or to the lanthanide or actinide groups in the Periodic Table of the Elements (new IUPAC version), X, same or different, is hydrogen, a halogen, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are hydrogen or alkyl groups; p is an integer of from 0 to 3, being equal to the oxidation state of the metal M minus 2.

The above metallocenes are particular useful in the polymerization of propylene.

35 Claims, 2 Drawing Sheets

METALLOCENE COMPOUNDS, PROCESS FOR THEIR PREPARATION AND THEIR USE IN CATALYTIC SYSTEMS FOR THE POLYMERIZATION OF OLEFINS

FIELD OF THE INVENTION

The present invention relates to a new class of metallocene compounds, to a catalyst for the polymerization of olefins containing them and to a polymerization process carried out in the presence of said catalyst. The invention also relates to the corresponding ligands useful as intermediates in the synthesis of said metallocene compounds, as well as to processes for preparing said ligands and said metallocene compounds.

DESCRIPTION OF THE PRIOR ART

Metallocene compounds with two cyclopentadienyl groups are known as catalyst components for the polymerization of olefins. European Patent 129,368, for instance, describes a catalyst system for the polymerization of olefins comprising (a) a bis-cyclopentadienyl coordination complex with a transition metal and (b) an alumoxane. The two cyclopentadienyl groups can be linked by a divalent group.

More recently, heterocyclic metallocene compounds used in the polymerization of alpha-olefins have been described. For example, U.S. Pat. No. 5,489,659 relates to a class of silicon-containing metallocene compounds for the polymerization of alpha-olefins wherein the silicon atom is part of a non-aromatic ring condensed to the cyclopentadienyl ring. Metallocenes of this type are used in the polymerization of propylene. The activity of these metallocene-based catalysts is not satisfactory.

In International application WO 98/22486 it is described a class of metallocenes containing a cyclopentadienyl radical directly coordinating the central metal atom, to which are fused one or more rings containing at least one heteroatom. These metallocenes, in combination with a suitable cocatalyst, are used in the polymerization of olefins, such as propylene. However, the molecular weights that can be obtained at polymerization temperatures of industrial interest are still too low for most utilization and the activity of those catalyst systems, when used in the polymerization of propylene, is not satisfactory.

It would be desirable to provide a novel class of metallocenes which, when used in catalysts for the polymerization of olefins, in particular of propylene, have high activity such that the amount of the catalyst remaining in the formed polymer is minimized, and which are capable of yielding polymers endowed with high molecular weights, narrow molecular weight distribution as well as a high degree of isotacticity and thus of cristallinity.

A novel class of metallocene compounds has now been unexpectedly found, which achieves the above and other results.

According to a first aspect, the present invention provides a metallocene compound of the general formula (I):

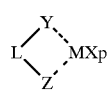

(I)

wherein
Y is a moiety of formula (II)

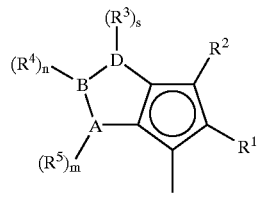

(II)

wherein
A, B and D, same or different from each other, are selected from an element of the groups 14 to 16 of the Periodic Table of the Elements (new IUPAC version), with the exclusion of nitrogen and oxygen;
$R^1$, $R^2$, $R^3$, $R^4$ and $R^5$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms; wherein two $R^3$ can form a ring comprising 4 to 8 atoms, and $R^3$ and $R^4$ can form a ring comprising 4 to 8 atoms, which can bear substituents; with the proviso that when s is 0 or when $R^3$ is hydrogen, $R^2$ is not hydrogen;
n, m and s are selected from 0, 1 and 2;
n, m and s being 0 when A, B and D are selected from an element of the group 16 of the Periodic Table of the Elements (new IUPAC version);
n, m and s being 1 when A, B and D are selected from an element of the group 15 of the Periodic Table of the Elements (new IUPAC version);
n, m and s being 1 or 2 when A, B and D are selected from an element of the group 14 of the Periodic Table of the Elements (new IUPAC version);
and wherein the ring containing A, B and D can have double bonds in any of the allowed positions;
Z is selected from a moiety of formula (II) as described above and from a moiety of formula (III):

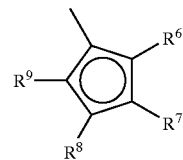

(III)

wherein $R^6$, $R^7$, $R^8$ and $R^9$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms, $R^7$ being different from hydrogen; optionally $R^6$ and $R^7$ can form a ring comprising 4 to 8 carbon atoms, which can bear substituents; and when Z is a moiety of formula (II), Y and Z can be the same or different from each other;
L is a divalent bridging group;
M is an atom of a transition metal selected from those belonging to group 3, 4, 5, 6 or to the lanthanide or actinide groups in the Periodic Table of the Elements (new IUPAC version),
X, same or different, is a hydrogen atom, a halogen atom, a $R^{10}$, $OR^{10}$, $OSO_2CF_3$, $OCOR^{10}$, $SR^{10}$, $NR^{10}{}_2$ or $PR^{10}{}_2$ group, wherein the substituents $R^{10}$ are defined as $R^7$;

p is an integer of from 0 to 3, being equal to the oxidation state of the metal M minus 2.

The transition metal M is preferably titanium, zirconium or hafnium. More preferably it is zirconium.

Preferably the substituents X are chlorine atoms or methyl groups.

Preferably the divalent bridging group L is =Si($R^{17}$)$_2$ or =C($R^{17}$)$_2$, wherein $R^{17}$, equal or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms, and wherein two $R^{17}$ can form a cycle comprising from 3 to 8 atoms.

More preferably the divalent bridging group L is selected from the group consisting of Si(CH$_3$)$_2$, Si(Phenyl)$_2$, CH$_2$ and C(CH$_3$)$_2$.

Preferably A is selected from sulfur, selenium, tellurium and polonium, more preferably it is sulfur.

Preferably B and D are selected from the group 14 of the Periodic Table of the Elements (new IUPAC version), more preferably they are carbon atoms.

When Z is a moiety of formula (III) it is preferably selected among those of formula (IV):

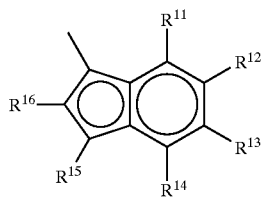

(IV)

wherein $R^{11}$, $R^{12}$, $R^{13}$, $R^{14}$, $R^{15}$ and $R^{16}$, same or different from each other, are selected from hydrogen, a $C_1$–$C_{20}$-alkyl $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms, optionally $R^{13}$ and $R^{14}$ can form a ring comprising 4 to 8 atoms which can bear substituents. Preferably $R^{14}$ and $R^{16}$ are different from hydrogen. More preferably $R^{14}$ is a $C_6$–$C_{20}$-aryl group, such as a phenyl or naphtyl group, and $R^{16}$ is a $C_1$–$C_{20}$-alkyl group, such as a methyl group. Non limiting examples of the metallocenes of the present invention are:

dimethylsilandiylbis-6-(3-methylcyclopentadienyl-[1,2-b]-thiophene)zirconium dichloride and methyl;
dimethylsilandiylbis-6-(4-methylcyclopentadienyl-[1,2-b]-thiophene)zirconium dichloride and methyl;
dimethylsilandiylbis-6-(4-isopropylcyclopentadienyl-[1,2-b]-thiophene)zirconium dichloride and methyl;
dimethylsilandiylbis-6-(4-ter-butylcyclopentadienyl-[1,2-b]-thiophene)zirconium dichloride and methyl;
dimethylsilandiylbis-6-(3-isopropylcyclopentadienyl-[1,2-b]-thiophene)zirconium dichloride and methyl;
dimethylsilandiylbis-6-(3-phenylcyclopentadienyl-[1,2-b]-thiophene)zirconium dichloride and methyl;
dimethylsilandiylbis-6-(2,5-dimethyl-3-phenylcyclopentadienyl-[1,2-b]-thiophene)zirconium dichloride and methyl;
dimethylsilandiylbis-6-[2,5-dimethyl-3-(2-methylphenyl)cyclopentadienyl-[1,2-b]-thiophene]zirconium dichloride and methyl;
dimethylsilandiylbis-6-[2,5-dimethyl-3-(2,4,6-trimethylphenyl)cyclopentadienyl-[1,2-b]-thiophene]zirconium dichloride and methyl;
dimethylsilandiylbis-6-[2,5-dimethyl-3-mesitylenecyclopentadienyl-[1,2-b]-thiophene]zirconium dichloride and methyl;
dimethylsilandiylbis-6-(2,4,5-trimethyl-3-phenylcyclopentadienyl-[1,2-b]-thiophene)zirconium dichloride and methyl;
dimethylsilandiylbis-6-(2,5-diethyl-3-phenylcyclopentadienyl-[1,2-b]-thiophene)zirconium dichloride and methyl;
dimethylsilandiylbis-6-(2,5-diisopropyl-3-phenylcyclopentadienyl-[1,2-b]-thiophene)zirconium dichloride and methyl;
dimethylsilandiylbis-6-(2,5-diter-butyl-3-phenylcyclopentadienyl-[1,2-b]-thiophene)zirconium dichloride and methyl;
dimethylsilandiylbis-6-(2,5-ditrimethylsilyl-3-phenylcyclopentadienyl-[1,2-b]-thiophene)zirconium dichloride and methyl;
dimethylsilandiylbis-6-(3-methylcyclopentadienyl-[1,2-b]-silole)zirconium dichloride and methyl;
dimethylsilandiylbis-6-(3-isopropylcyclopentadienyl-[1,2-b]-silole)zirconium dichloride and methyl;
dimethylsilandiylbis-6-(3-phenylcyclopentadienyl-[1,2-b]-silole)zirconium dichloride and methyl;
dimethylsilandiylbis-6-(2,5-dimethyl-3-phenylcyclopentadienyl-[1,2-b]-silole)zirconium dichloride and methyl;
dimethylsilandiylbis-6-[2,5-dimethyl-3-(2-methylphenyl)cyclopentadienyl-[1,2-b]-silole]zirconium dichloride and methyl;
dimethylsilandiylbis-6-[2,5-dimethyl-3-(2,4,6-trimethylphenyl)cyclopentadienyl-[1,2-b]-silole]zirconium dichloride and methyl;
dimethylsilandiylbis-6-[2,5-dimethyl-3-mesitylenecyclopentadienyl-[1,2-b]-silole]zirconium dichloride and methyl;
dimethylsilandiylbis-6-(2,4,5-trimethyl-3-phenylcyclopentadienyl-[1,2-b]-silole)zirconium dichloride and methyl;
dimethylsilandiylbis-6-(2,5-diethyl-3-phenylcyclopentadienyl-[1,2-b]-silole)zirconium dichloride and methyl;
dimethylsilandiylbis-6-(2,5-diisopropyl-3-phenylcyclopentadienyl-[1,2-b]-silole)zirconium dichloride and methyl;
dimethylsilandiylbis-6-(2,5-diter-butyl-3-phenylcyclopentadienyl-[1,2-b]-silole)zirconium dichloride and methyl;
dimethylsilandiylbis-6-(2,5-ditrimethylsilyl-3-phenylcyclopentadienyl-[1,2-b]-silole)zirconium dichloride and methyl;
dimethylsilandiylbis-6-(3-methylcyclopentadienyl-[1,2-b]-tellurophene)zirconium dichloride and methyl;
dimethylsilandiylbis-6-(3-isopropylcyclopentadienyl-[1,2-b]-tellurophene)zirconium dichloride and methyl;
dimethylsilandiylbis-6-(3-phenylcyclopentadienyl-[1,2-b]-tellurophene)zirconium dichloride and methyl;
dimethylsilandiylbis-6-(2,5-dimethyl-3-phenylcyclopentadienyl-[1,2-b]-tellurophene)zirconium dichloride and methyl;
dimethylsilandiylbis-6-[2,5-dimethyl-3-(2-methylphenyl)cyclopentadienyl-[1,2-b]-tellurophene]zirconium dichloride and methyl;
dimethylsilandiylbis-6-[2,5-dimethyl-3-(2,4,6-trimethylphenyl)cyclopentadienyl-[1,2-b]-tellurophene]zirconium dichloride and methyl;
dimethylsilandiylbis-6-[2,5-dimethyl-3-mesitylenecyclopentadienyl-[1,2-b]-tellurophene]zirconium dichloride and methyl;

dimethylsilandiylbis-6-(2,4,5-trimethyl-3-phenylcyclopentadienyl-[1,2-b]-tellurophene)zirconium dichloride and methyl;
dimethylsilandiylbis-6-(2,5-diethyl-3-phenylcyclopentadienyl-[1,2-b]-tellurophene)zirconium dichloride and methyl;
dimethylsilandiylbis-6-(2,5-diisopropyl-3-phenylcyclopentadienyl-[2-b]-tellurophene)zirconium dichloride and methyl;
dimethylsilandiylbis-6-(2,5-diter-butyl-3-phenylcyclopentadienyl-[1,2-b]-tellurophene)zirconium dichloride and methyl;
dimethylsilandiylbis-6-(2,5-ditrimethylsilyl-3-phenylcyclopentadienyl-[1,2-b]-tellurophene)zirconium dichloride and methyl;
dimethylsilandiylbis-6-(3-methylcyclopentadienyl-[1,2-b]-tellurophene)zirconium dichloride and methyl;
dimethylsilandiylbis-6-(3-isopropylcyclopentadienyl-[1,2-b]-tellurophene)zirconium dichloride and methyl;
dimethylsilandiylbis-6-(3-phenylcyclopentadienyl-[1,2-b]-tellurophene)zirconium dichloride and methyl;
dimethylsilandiylbis-6-(2,5-dimethyl-3-phenylcyclopentadienyl-[1,2-b]-tellurophene)zirconium dichloride and methyl;
dimethylsilandiylbis-6-[2,5-dimethyl-3-(2-methylphenyl)cyclopentadienyl-[1,2-b]-tellurophene]zirconium dichloride and methyl;
dimethylsilandiylbis-6-[2,5-dimethyl-3-(2,4,6-trimethylphenyl)cyclopentadienyl-[1,2-b]-tellurophene]zirconium dichloride and methyl;
dimethylsilandiylbis-6-[2,5-dimethyl-3-mesitylenecyclopentadienyl-[1,2-b]-tellurophene]zirconium dichloride and methyl;
dimethylsilandiylbis-6-(2,4,5-trimethyl-3-phenylcyclopentadienyl-[1,2-b]-tellurophene)zirconium dichloride and methyl;
dimethylsilandiylbis-6-(2,5-diethyl-3-phenylcyclopentadienyl-[1,2-b]-tellurophene)zirconium dichloride and methyl;
dimethylsilandiylbis-6-(2,5-diisopropyl-3-phenylcyclopentadienyl-[1,2-b]-tellurophene)zirconium dichloride and methyl;
dimethylsilandiylbis-6-(2,5-diter-butyl-3-phenylcyclopentadienyl-[1,2-b]-tellurophene)zirconium dichloride and methyl;
dimethylsilyl-6-(2,5-dimethyl-3-phenylcyclopentadienyl-[1,2-b]-tellurophene)-1-(2-methyl-4-phenylindenyl)zirconium dichloride and methyl;
dimethylsilandiylbis-6-(2,5-ditrimethylsilyl-3-phenylcyclopentadienyl-[1,2-b]-tellurophene)zirconium dichloride and methyl;
dimethylsilandiylbis-6-(3-methylcyclopentadienyl-[1,2-b]-phosphole)zirconium dichloride and methyl;
dimethylsilandiylbis-6-(3-isopropylcyclopentadienyl-[1,2-b]-phosphole)zirconium dichloride and methyl;
dimethylsilandiylbis-6-(3-phenylcyclopentadienyl-[1,2-b]-phosphole)zirconium dichloride and methyl;
dimethylsilandiylbis-6-(2,5-dimethyl-3-phenylcyclopentadienyl-[1,2-b]-phosphole)zirconium dichloride and methyl;
dimethylsilandiylbis-6-[2,5-dimethyl-3-(2-methylphenyl)cyclopentadienyl-[1,2-b]-phosphole]zirconium dichloride and methyl;
dimethylsilandiylbis-6-[2,5-dimethyl-3-(2,4,6-trimethylphenyl)cyclopentadienyl-[1,2-b]-phosphole]zirconium dichloride and methyl;
dimethylsilandiylbis-6-[2,5-dimethyl-3-mesitylenecyclopentadienyl-[1,2-b]-phosphole]zirconium dichloride and methyl;
dimethylsilandiylbis-6-(2,4,5-trimethyl-3-phenylcyclopentadienyl-[1,2-b]-phosphole)zirconium dichloride and methyl;
dimethylsilandiylbis-6-(2,5-diethyl-3-phenylcyclopentadienyl-[1,2-b]-phosphole)zirconium dichloride and methyl;
dimethylsilandiylbis-6-(2,5-diisopropyl-3-phenylcyclopentadienyl-[1,2-b]-phosphole)zirconium dichloride and methyl;
dimethylsilandiylbis-6-(2,5-diter-butyl-3-phenylcyclopentadienyl-[1,2-b]-phosphole)zirconium dichloride and methyl;
dimethylsilyl-6-(2,5-dimethyl-3-phenylcyclopentadienyl-[1,2-b]-phosphole)-1-(2-methyl-4-phenylindenyl)zirconium dichloride and methyl;
dimethylsilandiylbis-6-(2,5-ditrimethylsilyl-3-phenylcyclopentadienyl-[1,2-b]-phosphole)zirconium dichloride and methyl;
isopropylidenebis-6-(3-methylcyclopentadienyl-[1,2-b]-thiophene)zirconium dichloride and methyl;
isopropylidenebis-6-(3-isopropylcyclopentadienyl-[1,2-b]-thiophene)zirconium dichloride and methyl;
isopropylidenebis-6-(3-phenylcyclopentadienyl-[1,2-b]-thiophene)zirconium dichloride and methyl;
isopropylidenebis-6-(2,5-dimethyl-3-phenylcyclopentadienyl-[1,2-b]-thiophene)zirconium dichloride and methyl;
isopropylidenebis-6-[2,5-dimethyl-3-(2-methylphenyl)cyclopentadienyl-[1,2-b]-thiophene]zirconium dichloride and methyl;
isopropylidenebis-6-[2,5-dimethyl-3-(2,4,6-trimethylphenyl)cyclopentadienyl-[1,2-b]-thiophene]zirconium dichloride and methyl;
isopropylidenebis-6-[2,5-dimethyl-3-mesitylenecyclopentadienyl-[1,2-b]-thiophene]zirconium dichloride and methyl;
isopropylidenebis-6-(2,4,5-trimethyl-3-phenylcyclopentadienyl-[1,2-b]-thiophene)zirconium dichloride and methyl;
isopropylidenebis-6-(2,5-diethyl-3-phenylcyclopentadienyl-[1,2-b]-thiophene)zirconium dichloride and methyl;
isopropylidenebis-6-(2,5-diisopropyl-3-phenylcyclopentadienyl-[1,2-b]-thiophene)zirconium dichloride and methyl;
isopropylidenebis-6-(2,5-diter-butyl-3-phenylcyclopentadienyl-[1,2-b]-thiophene)zirconium dichloride and methyl;
isopropylidenebis-6-(2,5-ditrimethylsilyl-3-phenylcyclopentadienyl-[1,2-b]-thiophene)zirconium dichloride and methyl;
isopropylidenebis-6-(3-methylcyclopentadienyl-[1,2-b]-silole)zirconium dichloride and methyl;
isopropylidenebis-6-(3-isopropylcyclopentadienyl-[1,2-b]-silole)zirconium dichloride and methyl;
isopropylidenebis-6-(3-phenylcyclopentadienyl-[1,2-b]-silole)zirconium dichloride and methyl;
isopropylidenebis-6-(2,5-dimethyl-3-phenylcyclopentadienyl-[1,2-b]-silole)zirconium dichloride and methyl;
isopropylidenebis-6-[2,5-dimethyl-3-(2-methylphenyl)cyclopentadienyl-[1,2-b]-silole]zirconium dichloride and methyl;
isopropylidenebis-6-[2,5-dimethyl-3-(2,4,6-trimethylphenyl)cyclopentadienyl-[1,2-b]-silole]zirconium dichloride and methyl;
isopropylidenebis-6-[2,5-dimethyl-3-mesitylenecyclopentadienyl-[1,2-b]-silole]zirconium dichloride and methyl;

isopropylidenebis-6-(2,4,5-trimethyl-3-phenylcyclopentadienyl-[1,2-b]-silole)zirconium dichloride and methyl;
isopropylidenebis-6-(2,5-diethyl-3-phenylcyclopentadienyl-[1,2-b]-silole)zirconium dichloride and methyl;
isopropylidenebis-6-(2,5-diisopropyl-3-phenylcyclopentadienyl-[1,2-b]-silole)zirconium dichloride and methyl;
isopropylidenebis-6-(2,5-diter-butyl-3-phenylcyclopentadienyl-[1,2-b]-silole)zirconium dichloride and methyl;
isopropylidenebis-6-(2,5-ditrimethylsilyl-3-phenylcyclopentadienyl-[1,2-b]-silole)zirconium dichloride and methyl;
isopropylidenebis-6-(3-methylcyclopentadienyl-[1,2-b]-tellurophene)zirconium dichloride and methyl;
isopropylidenebis-6-(3-isopropylcyclopentadienyl-[1,2-b]-tellurophene)zirconium dichloride and methyl;
isopropylidenebis-6-(3-phenylcyclopentadienyl-[1,2-b]-tellurophene)zirconium dichloride and methyl;
isopropylidenebis-6-(2,5-dimethyl-3-phenylcyclopentadienyl-[1,2-b]-tellurophene)zirconium dichloride and methyl;
isopropylidenebis-6-[2,5-dimethyl-3-(2-methylphenyl)cyclopentadienyl-[1,2-b]-tellurophene]zirconium dichloride and methyl;
isopropylidenebis-6-[2,5-dimethyl-3-(2,4,6-trimethylphenyl)cyclopentadienyl-[1,2-b]-tellurophene]zirconium dichloride and methyl;
isopropylidenebis-6-[2,5-dimethyl-3-mesitylenecyclopentadienyl-[1,2-b]-tellurophene]zirconium dichloride and methyl;
isopropylidenebis-6-(2,4,5-trimethyl-3-phenylcyclopentadienyl-[1,2-b]-tellurophene)zirconium dichloride and methyl;
isopropylidenebis-6-(2,5-diethyl-3-phenylcyclopentadienyl-[1,2-b]-tellurophene)zirconium dichloride and methyl;
isopropylidenebis-6-(2,5-diisopropyl-3-phenylcyclopentadienyl-[1,2-b]-tellurophene)zirconium dichloride and methyl;
isopropylidenebis-6-(2,5-diter-butyl-3-phenylcyclopentadienyl-[1,2-b]-tellurophene)zirconium dichloride and methyl;
isopropylidenebis-6-(2,5-ditrimethylsilyl-3-phenylcyclopentadienyl-[1,2-b]-tellurophene)zirconium dichloride and methyl;
isopropylidenebis-6-(3-methylcyclopentadienyl-[1,2-b]-tellurophene)zirconium dichloride and methyl;
isopropylidenebis-6-(3-isopropylcyclopentadienyl-[1,2-b]-tellurophene)zirconium dichloride and methyl;
isopropylidenebis-6-(3-phenylcyclopentadienyl-[1,2-b]-tellurophene)zirconium dichloride and methyl;
isopropylidenebis-6-(2,5-dimethyl-3-phenylcyclopentadienyl-[1,2-b]-tellurophene)zirconium dichloride and methyl;
isopropylidenebis-6-[2,5-dimethyl-3-(2-methylphenyl)cyclopentadienyl-[1,2-b]-tellurophene]zirconium dichloride and methyl;
isopropylidenebis-6-[2,5-dimethyl-3-(2,4,6-trimethylphenyl)cyclopentadienyl-[1,2-b]-tellurophene]zirconium dichloride and methyl;
isopropylidenebis-6-[2,5-dimethyl-3-mesitylenecyclopentadienyl-[1,2-b]-tellurophene]zirconium dichloride and methyl;
isopropylidenebis-6-(2,4,5-trimethyl-3-phenylcyclopentadienyl-[1,2-b]-tellurophene)zirconium dichloride and methyl;
isopropylidenebis-6-(2,5-diethyl-3-phenylcyclopentadienyl-[1,2-b]-tellurophene)zirconium dichloride and methyl;
isopropylidenebis-6-(2,5-diisopropyl-3-phenylcyclopentadienyl-[1,2-b]-tellurophene)zirconium dichloride and methyl;
isopropylidenebis-6-(2,5-diter-butyl-3-phenylcyclopentadienyl-[1,2-b]-tellurophene)zirconium dichloride and methyl;
isopropylidenebis-6-(2,5-ditrimethylsilyl-3-phenylcyclopentadienyl-[1,2-b]-tellurophene)zirconium dichloride and methyl;
isopropylidenebis-6-(3-methylcyclopentadienyl-[1,2-b]-phosphole)zirconium dichloride and methyl;
isopropylidenebis-6-(3-isopropylcyclopentadienyl-[1,2-b]-phosphole)zirconium dichloride and methyl;
isopropylidenebis-6-(3-phenylcyclopentadienyl-[1,2-b]-phosphole)zirconium dichloride and methyl;
isopropylidenebis-6-(2,5-dimethyl-3-phenylcyclopentadienyl-[1,2-b]-phosphole)zirconium dichloride and methyl;
isopropylidenebis-6-[2,5-dimethyl-3-(2-methylphenyl)cyclopentadienyl-[1,2-b]-phosphole]zirconium dichloride and methyl;
isopropylidenebis-6-[2,5-dimethyl-3-(2,4,6-trimethylphenyl)cyclopentadienyl-[1,2-b]-phosphole]zirconium dichloride and methyl;
isopropylidenebis-6-[2,5-dimethyl-3-mesitylenecyclopentadienyl-[1,2-b]-phosphole]zirconium dichloride and methyl;
isopropylidenebis-6-(2,4,5-trimethyl-3-phenylcyclopentadienyl-[1,2-b]-phosphole)zirconium dichloride and methyl;
isopropylidenebis-6-(2,5-diethyl-3-phenylcyclopentadienyl-[1,2-b]-phosphole)zirconium dichloride and methyl;
isopropylidenebis-6-(2,5-diisopropyl-3-phenylcyclopentadienyl-[1,2-b]-phosphole)zirconium dichloride and methyl;
isopropylidenebis-6-(2,5-diter-butyl-3-phenylcyclopentadienyl-[1,2-b]-phosphole)zirconium dichloride and methyl;
isopropylidenebis-6-(2,5-ditrimethylsilyl-3-phenylcyclopentadienyl-[1,2-b]-phosphole)zirconium dichloride and methyl;
dimethylsilandiylbis-5-(2-methylcyclopentadienyl-[c]-thiophene)zirconium dichloride and methyl;
dimethylsilandiylbis-5-(2-isopropylcyclopentadienyl-[c]-thiophene)zirconium dichloride and methyl;
dimethylsilandiylbis-5-(2-phenylcyclopentadienyl-[c]-thiophene)zirconium dichloride and methyl;
dimethylsilandiylbis-5-(2,4-dimethyl-cyclopentadienyl-[c]-thiophene)zirconium dichloride and methyl;
dimethylsilandiylbis-5-[(2-methylphenyl)-4-methylcyclopentadienyl-[c]-thiophene]zirconium dichloride and methyl;
dimethylsilandiylbis-5-[2-(2,4,6-trimethylphenyl)cyclopentadienyl-[c]-thiophene]zirconium dichloride and methyl;
dimethylsilandiylbis-5-[2-mesitylene-4-methylcyclopentadienyl-[c]-thiophene]zirconium dichloride and methyl;
dimethylsilandiylbis-5-(2,4-diisopropyl-cyclopentadienyl-[c]-thiophene)zirconium dichloride and methyl;
dimethylsilandiylbis-5-(2,4-diter-butyl-cyclopentadienyl-[c]-thiophene)zirconium dichloride and methyl;
dimethylsilandiylbis-5-(2,4-ditrimethylsilyl-cyclopentadienyl-[c]-thiophene)zirconium dichloride and methyl;

dimethylsilandiylbis-5-(2-methylcyclopentadienyl-[c]-phosphole)zirconium dichloride and methyl;
dimethylsilandiylbis-5-(2-isopropylcyclopentadienyl-[c]-phosphole)zirconium dichloride and methyl;
dimethylsilandiylbis-5-(2-phenylcyclopentadienyl-[c]-phosphole)zirconium dichloride and methyl;
dimethylsilandiylbis-5-(2,4-dimethyl-cyclopentadienyl-[c]-phosphole)zirconium dichloride and methyl;
dimethylsilandiylbis-5-[(2-methylphenyl)-4-methylcyclopentadienyl-[c]-phosphole]zirconium dichloride and methyl;
dimethylsilandiylbis-5-[2-(2,4,6-trimethylphenyl)cyclopentadienyl-[c]-phosphole]zirconium dichloride and methyl;
dimethylsilandiylbis-5-[2-mesitylene-4-methylcyclopentadienyl-[c]-phosphole]zirconium dichloride and methyl;
dimethylsilandiylbis-5-(2,4-diisopropyl-cyclopentadienyl-[c]-phosphole)zirconium dichloride and methyl;
dimethylsilandiylbis-5-(2,4-diter-butyl-cyclopentadienyl-[c]-phosphole)zirconium dichloride and methyl;
dimethylsilandiylbis-5-(2,4-ditrimethylsilyl-cyclopentadienyl-[c]-phosphole)zirconium dichloride and methyl;
dimethylsilandiylbis-5-(2-methylcyclopentadienyl-[c]-tellurophene)zirconium dichloride and methyl;
dimethylsilandiylbis-5-(2-isopropylcyclopentadienyl-[c]-tellurophene)zirconium dichloride and methyl;
dimethylsilandiylbis-5-(2-phenylcyclopentadienyl-[c]-tellurophene)zirconium dichloride and methyl;
dimethylsilandiylbis-5-(2,4-dimethyl-cyclopentadienyl-[c]-tellurophene)zirconium dichloride and methyl;
dimethylsilandiylbis-5-[(2-methylphenyl)-4-methylcyclopentadienyl-[c]-tellurophene]zirconium dichloride and methyl;
dimethylsilandiylbis-5-[2-(2,4,6-trimethylphenyl)cyclopentadienyl-[c]-tellurophene]zirconium dichloride and methyl;
dimethylsilandiylbis-5-[2-mesitylene-4-methylcyclopentadienyl-[c]-tellurophene]zirconium dichloride and methyl;
dimethylsilandiylbis-5-(2,4-diisopropyl-cyclopentadienyl-[c]-tellurophene)zirconium dichloride and methyl;
dimethylsilandiylbis-5-(2,4-diter-butyl-cyclopentadienyl-[c]-tellurophene)zirconium dichloride and methyl;
dimethylsilyl-5-(2,4-dimethyl-cyclopentadienyl-[c]-tellurophene)-1-(2-methyl-4-phenylindenyl)zirconium dichloride and methyl;
dimethylsilandiylbis-5-(2,4-ditrimethylsilyl-cyclopentadienyl-[c]-tellurophene)zirconium dichloride and methyl;
methylenebis-5-(2-methylcyclopentadienyl-[c]-thiophene)zirconium dichloride and methyl;
methylenebis-5-(2-isopropylcyclopentadienyl-[c]-thiophene)zirconium dichloride and methyl;
methylenebis-5-(2-phenylcyclopentadienyl-[c]-thiophene)zirconium dichloride and methyl;
methylenebis-5-(2,4-dimethyl-cyclopentadienyl-[c]-thiophene)zirconium dichloride and methyl;
methylenebis-5-[(2-methylphenyl)-4-methylcyclopentadienyl-[c]-thiophene]zirconium dichloride and methyl;
methylenebis-5-[2-(2,4,6-trimethylphenyl)cyclopentadienyl-[c]-thiophene]zirconium dichloride and methyl;
methylenebis-5-[2-mesitylene-4-methylcyclopentadienyl-[c]-thiophene]zirconium dichloride and methyl;
methylenebis-5-(2,4-diisopropyl-cyclopentadienyl-[c]-thiophene)zirconium dichloride and methyl;
methylenebis-5-(2,4-diter-butyl-cyclopentadienyl-[c]-thiophene)zirconium dichloride and methyl;
methylenebis-5-(2,4-ditrimethylsilyl-cyclopentadienyl-[c]-thiophene)zirconium dichloride and methyl;
methylenebis-5-(2-methylcyclopentadienyl-[c]-phosphole)zirconium dichloride and methyl;
methylenebis-5-(2-isopropylcyclopentadienyl-[c]-phosphole)zirconium dichloride and methyl;
methylenebis-5-(2-phenylcyclopentadienyl-[c]-phosphole)zirconium dichloride and methyl;
methylenebis-5-(2,4-dimethyl-cyclopentadienyl-[c]-phosphole)zirconium dichloride and methyl;
methylenebis-5-[(2-methylphenyl)-4-methylcyclopentadienyl-[c]-phosphole]zirconium dichloride and methyl;
methylenebis-5-[2-(2,4,6-trimethylphenyl)cyclopentadienyl-[c]-phosphole]zirconium dichloride and methyl;
methylenebis-5-[2-mesitylene-4-methylcyclopentadienyl-[c]-phosphole]zirconium dichloride and methyl;
methylenebis-5-(2,4-diisopropyl-cyclopentadienyl-[c]-phosphole)zirconium dichloride and methyl;
methylenebis-5-(2,4-diter-butyl-cyclopentadienyl-[c]-phosphole)zirconium dichloride and methyl;
methylenebis-5-(2,4-ditrimethylsilyl-cyclopentadienyl-[c]-phosphole)zirconium dichloride and methyl;
methylenebis-5-(2-methylcyclopentadienyl-[c]-tellurophene)zirconium dichloride and methyl;
methylenebis-5-(2-isopropylcyclopentadienyl-[c]-tellurophene)zirconium dichloride and methyl;
methylenebis-5-(2-phenylcyclopentadienyl-[c]-tellurophene)zirconium dichloride and methyl;
methylenebis-5-(2,4-dimethyl-cyclopentadienyl-[c]-tellurophene)zirconium dichloride and methyl;
methylenebis-5-[(2-methylphenyl)-4-methylcyclopentadienyl-[c]-tellurophene]zirconium dichloride and methyl;
methylenebis-5-[2-(2,4,6-trimethylphenyl)cyclopentadienyl-[c]-tellurophene]zirconium dichloride and methyl;
methylenebis-5-[2-mesitylene-4-methylcyclopentadienyl-[c]-tellurophene]zirconium dichloride and methyl;
methylenebis-5-(2,4-diisopropyl-cyclopentadienyl-[c]-tellurophene)zirconium dichloride and methyl;
methylenebis-5-(2,4-diter-butyl-cyclopentadienyl-[c]-tellurophene)zirconium dichloride and methyl;
dimethylsilyl-5-(2,4-dimethyl-cyclopentadienyl-[c]-tellurophene)-1-(2-methyl-4-phenylindenyl)zirconium dichloride and methyl;
methylenebis-5-(2,4-ditrimethylsilyl-cyclopentadienyl-[c]-tellurophene)zirconium dichloride and methyl;
dimethylsilandiylbis-4-(cyclopentadienyl-[2,1-b]-thiophene)zirconium dichloride and methyl;
dimethylsilandiylbis-4-(2-methylcyclopentadienyl-[2,1-b]-thiophene)zirconium dichloride and methyl;
dimethylsilandiylbis-4-(2,5-dimethylcyclopentadienyl-[2,1-b]-thiophene)zirconium dichloride and methyl;
dimethylsilandiylbis-4-(2,5-diisopropylcyclopentadienyl-[2,1-b]-thiophene)zirconium dichloride and methyl;
dimethylsilandiylbis-4-(2,5-diter-butylcyclopentadienyl-[2,1-b]-thiophene)zirconium dichloride and methyl;
dimethylsilandiylbis-4-(2,5-ditrimethylsilylcyclopentadienyl-[2,1-b]-thiophene)zirconium dichloride and methyl;
dimethylsilyl-4-(2,5-ditrimethylsilylcyclopentadienyl-[2,1-b]-thiophene)-1-(2-methyl-4-phenyl)zirconium dichloride and methyl;

dimethylsilandiylbis-4-(cyclopentadienyl-[2,1-b]-tellurophene)zirconium dichloride and methyl;
dimethylsilandiylbis-4-(2-methylcyclopentadienyl-[2,1-b]-tellurophene)zirconium dichloride and methyl;
dimethylsilandiylbis-4-(2,5-dimethylcyclopentadienyl-[2,1-b]-tellurophene)zirconium dichloride and methyl;
dimethylsilandiylbis-4-(2,5-diisopropylcyclopentadienyl-[2,1-b]-tellurophene)zirconium dichloride and methyl;
dimethylsilandiylbis-4-(2,5-diter-butylcyclopentadienyl-[2,1-b]-tellurophene)zirconium dichloride and methyl;
dimethylsilandiylbis-4-(2,5-ditrimethylsilylcyclopentadienyl-[2,1-b]-tellurophene)zirconium dichloride and methyl;
dimethylsilandiyl-6-(2,5-dimethyl-3-phenylcyclopentadienyl-[1,2-b]-thiophene)(3-methylcyclopentadienyl)zirconium dichloride and methyl;
dimethylsilandiyl-6-(2,5-dimethyl-3-phenylcyclopentadienyl-[1,2-b]-thiophene)(3-ter-butylcyclopentadienyl)zirconium dichloride and methyl.
dimethylsilandiyl-6-(2,5-dimethyl-3-phenylcyclopentadienyl-[1,2-b]-thiophene)-1-(2-methyl-4-phenylindenyl)zirconium dichloride and methyl;
dimethylsilandiyl-6-(2,5-dimethyl-3-phenylcyclopentadienyl-[1,2-b]-thiophene)-1-(benzoindenyl)zirconium dichloride and methyl;
dimethylsilandiyl-6-(2,5-dimethyl-3-phenylcyclopentadienyl-[1,2-b]-silole)-1-(2-methyl-4-phenylindenyl)zirconium dichloride and methyl;
dimethylsilandiyl-6-(2,5-dimethyl-3-phenylcyclopentadienyl-[1,2-b]-silole)-1-(benzoindenyl)zirconium dichloride and methyl;
dimethylsilandiyl-6-(2,5-dimethyl-3-phenylcyclopentadienyl-[1,2-b]-tellurophene)-1-(2-methyl-4-phenylindenyl)zirconium dichloride and methyl;
dimethylsilandiyl-6-(2,5-dimethyl-3-phenylcyclopentadienyl-[1,2-b]-thiophene)-1-(2-methyl-4-phenylindenyl)zirconium dichloride and methyl;
dimethylsilandiyl-6-(2,5-dimethyl-3-phenylcyclopentadienyl-[1,2-b]-silole)-1-(2-methyl-4-phenylindenyl)zirconium dichloride and methyl;
dimethylsilandiyl-6-(2,5-dimethyl-3-phenylcyclopentadienyl-[1,2-b]-tellurophene)-1-(2-methyl-4-phenylindenyl)zirconium dichloride and methyl;
dimethylsilandiyl-6-(2,5-dimethyl-3-phenylcyclopentadienyl-[1,2-b]-phosphole)-1-(2-methyl-4-phenylindenyl)zirconium dichloride and methyl;
dimethylsilandiyl-6-(2,5-dimethyl-3-phenylcyclopentadienyl-[1,2-b]-phosphole)-1-(benzoindenyl)zirconium dichloride and methyl;
dimethylsilandiyl-5-(2,4-dimethyl-cyclopentadienyl-[c]-thiophene)-1-(2-methyl-4-phenylindenyl)zirconium dichloride and methyl;
dimethylsilandiyl-5-(2,4-dimethyl-cyclopentadienyl-[c]-phosphole)-1-(2-methyl-4-phenylindenyl)zirconium dichloride and methyl;
dimethylsilandiyl-5-(2,4-dimethyl-cyclopentadienyl-[c]-thiophene)-1-(2-methyl-4-phenylindenyl)zirconium dichloride and methyl;
dimethylsilandiyl-5-(2,4-dimethyl-cyclopentadienyl-[c]-phosphole)-1-(2-methyl-4-phenylindenyl)zirconium dichloride and methyl;
dimethylsilandiyl-5-(2,4-dimethyl-cyclopentadienyl-[c]-phosphole)-1-(benzoindenyl)zirconium dichloride and methyl;
dimethylsilandiyl-4-(2,5-ditrimethylsilylcyclopentadienyl-[2,1-b]-tellurophene)-1-(2-methyl-4-phenyl)zirconium dichloride and methyl.

An interesting class of metallocene compounds according to the present invention is that of formula (I) wherein both Y and Z are a moiety of formula (II), $R^1$ is a $C_1$–$C_{20}$-alkyl group, preferably a methyl group, $R^2$ is hydrogen, $R^3$ is different from hydrogen, B and D are carbon atoms, A is an element of the group 16 of the Periodic Table of the Elements (new IUPAC version), preferably sulphur, m is 0, n and s are 1. Preferably $R^3$ is a $C_6$–$C_{20}$-aryl group, such as a phenyl group or a naphthyl group, or a $C_7$–$C_{20}$-alkylaryl group wherein the alkyl group is ortho-substituted to the aryl substituent, such as an ortho-methylphenyl group. Preferably $R^4$ is different from hydrogen. Preferably $R^5$ is a hydrogen.

In this class of metallocenes according to the invention the ring that comprises the heteroatom contains an additional double bond and thus has an aromatic character. Non limiting examples of said class are:

dimethylsilandiylbis-6-(2,5-dimethyl-3-phenylcyclopentadienyl-[1,2-b]-thiophene)zirconium dichloride,
dimethylsilandiylbis-6-(3,5-dimethyl-cyclopentadienyl-[1,2-b]-thiophene)zirconium dichloride and
dimethylsilandiylbis-6-[2,5-dimethyl-3-(2'-methylphenylcyclopentadienyl-[1,2-b]-thiophene]zirconium dichloride.

Another particular advantageous class of metallocenes according to the present invention are those wherein both Y and Z are a moiety of formula (II), L is a $=C(R^{17})_2$ group, $R^1$ is a hydrogen atom, $R^2$ is different from hydrogen. Non limiting examples of said class are:

isopropylidenebis-6-(4-methylcyclopentadienyl-[1,2-b]-thiophene)zirconium dichloride and methyl;
isopropylidenebis-6-(4-isopropylcyclopentadienyl-[1,2-b]-thiophene)zirconium dichloride and methyl;
isopropylidenebis-6-(4-terbutylcyclopentadienyl-[1,2-b]-thiophene)zirconium dichloride and methyl;
isopropylidenebis-6-(4-phenylclopentadienyl-[1,2-b]-thiophene)zirconium dichloride and methyl;
methylenebis-6-(4-methylcyclopentadienyl-[1,2-b]-thiophene)zirconium dichloride and methyl;
methylenebis-6-(4-isopropylcyclopentadienyl-[1,2-b]-thiophene)zirconium dichloride and methyl;
methylenebis-6-(4-terbutylcyclopentadienyl-[1,2-b]-thiophene)zirconium dichloride and methyl;
methylenebis-6-(4-phenylclopentadienyl-[1,2-b]-thiophene)zirconium dichloride and methyl.

Yet another particular advantageous class of metallocene compound according to the present invention corresponds to formula (I) wherein both Y and Z are a moiety of formula (II), m is 2 and $R^5$ is not hydrogen.

Non limiting examples of said class are:

dimethylsilandiylbis-6-(1,1,2,5-tetramethyl-3-phenylcyclopentadienyl-[1,2-b]-silole)zirconium dichloride and methyl;
dimethylsilandiylbis-6-(1,1,2,5-tetramethyl-3-phenylcyclopentadienyl-[1,2-b]-cyclopentadien)zirconium dichloride and methyl;
isopropylidenebis-6-(1,1,2,5-tetramethyl-3-phenylcyclopentadienyl-[1,2-b]-silole)zirconium dichloride and methyl;
isopropylidenebis-6-(1,1,2,5-tetramethyl-3-phenylcyclopentadienyl-[1,2-b]-cyclopentadien)zirconium dichloride and methyl;

According to another aspect of the present invention it is provided a class of ligands of formula (V):

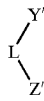

(V)

wherein Y' is a moiety of formula (VI):

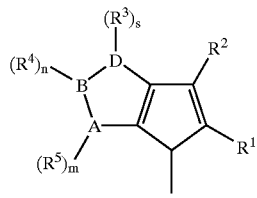

(VI)

and/or its double bond isomers;

$R^1$, $R^2$, $R^3$, $R^4$, A, B, D, n, m and s are defined as described above;

Z' is selected from a moiety of formula (VI) and from a moiety of formula (VII):

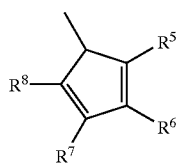

(VII)

and/or its double bond isomers;

$R^5$, $R^6$, $R^7$ and $R^8$ are defined as described above;

when Z' is equal to Y', A, B and D in Y' and Z' can be the same or different from each other;

L is a divalent bridge as defined above.

Preferably Z' is equal to Y'.

Preferably $R^1$ and $R^4$ are $C_1$–$C_{20}$-alkyl groups, $R^2$ is hydrogen, $R^3$ is a $C_6$–$C_{20}$-aryl or a $C_7$–$C_{20}$-alkylaryl group.

Preferably B and D are selected from the group 14 of the Periodic Table of the Elements (new IUPAC version), more preferably are carbon atoms.

Preferably A is selected from sulphur, selenium, tellurium and polonium, more preferably it is sulphur.

Preferably the divalent bridging group L is $(CH_3)_2Si=$, $Ph_2Si=$, $CH_2C=$ or $(CH_3)_2C=$.

Preferably n and s are 1 and m is 0.

More preferably $R^1$ and $R^4$ are methyl groups and $R^3$ is a $C_6$–$C_{20}$-aryl group or $C_7$–$C_{20}$-alkylaryl group, the alkyl substituent being on the ortho-position of the aryl group.

When Z is different from Y it is preferred a moiety of formula (VIII):

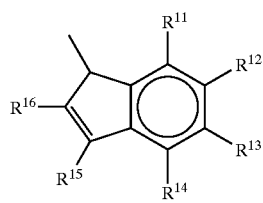

(VIII)

and/or its double bond isomers;

wherein $R^{11}$, $R^{12}$, $R^{13}$, $R^{14}$, $R^{15}$ and $R^{16}$ are defined as above;

Non limiting examples of said class are:

dimethylbis-6-(3-methylcyclopentadienyl-[1,2-b]-thiophene)silane;
dimethylbis-6-(3-isopropylcyclopentadienyl-[1,2-b]-thiophene)silane;
dimethylbis-6-(3-phenylcyclopentadienyl-[1,2-b]-thiophene)silane;
dimethylbis-6-(2,5-dimethyl-3-phenylcyclopentadienyl-[1,2-b]-thiophene)silane;
dimethylbis-6-[2,5-dimethyl-3-(2-methylphenyl)cyclopentadienyl-[1,2-b]-thiophene]silane;
dimethylbis-6-[2,5-dimethyl-3-(2,4,6-trimethylphenyl)cyclopentadienyl-[1,2-b]-thiophene]silane;
dimethylbis-6-[2,5-dimethyl-3-mesitylenecyclopentadienyl-[1,2-b]-thiophene]silane;
dimethylbis-6-(2,4,5-trimethyl-3-phenylcyclopentadienyl-[1,2-b]-thiophene)silane;
dimethylbis-6-(2,5-diethyl-3-phenylcyclopentadienyl-[1,2-b]-thiophene)silane;
dimethylbis-6-(2,5-diisopropyl-3-phenylcyclopentadienyl-[1,2-b]-thiophene)silane;
dimethylbis-6-(2,5-diter-butyl-3-phenylcyclopentadienyl-[1,2-b]-thiophene)silane;
dimethylbis-6-(2,5-ditrimethylsilyl-3-phenylcyclopentadienyl-[1,2-b]-thiophene)silane;
dimethylbis-6-(3-methylcyclopentadienyl-[1,2-b]-silole)silane;
dimethylbis-6-(3-isopropylcyclopentadienyl-[1,2-b]-silole)silane;
dimethylbis-6-(3-phenylcyclopentadienyl-[1,2-b]-silole)silane;
dimethylbis-6-(2,5-dimethyl-3-phenylcyclopentadienyl-[1,2-b]-silole)silane;
dimethylbis-6-[2,5-dimethyl-3-(2-methylphenyl)cyclopentadienyl-[1,2-b]-silole]silane;
dimethylbis-6-[2,5-dimethyl-3-(2,4,6-trimethylphenyl)cyclopentadienyl-[1,2-b]-silole]silane;
dimethylbis-6-[2,5-dimethyl-3-mesitylenecyclopentadienyl-[1,2-b]-silole)silane;
dimethylbis-6-(2,4,5-trimethyl-3-phenylcyclopentadienyl-[1,2-b]-silole)silane;
dimethylbis-6-(2,5-diethyl-3-phenylcyclopentadienyl-[1,2-b]-silole)silane;
dimethylbis-6-(2,5-diisopropyl-3-phenylcyclopentadienyl-[1,2-b]-silole)silane;
dimethylbis-6-(2,5-diter-butyl-3-phenylcyclopentadienyl-[1,2-b]-silole)silane;
dimethylsilyl-6-(2,5-dimethyl-3-phenylcyclopentadienyl-[1,2-b]-silole)-1-(2-methyl-4-phenylindenyl)silane;
dimethylbis-6-(2,5-ditrimethylsilyl-3-phenylcyclopentadienyl-[1,2-b]-silole)silane;
dimethylbis-6-(3-methylcyclopentadienyl-[1,2-b]tellurophene)silane;
dimethylbis-6-(3-isopropylcyclopentadienyl-[1,2-b]-tellurophene)silane;
dimethylbis-6-(3-phenylcyclopentadienyl-[1,2-b]-tellurophene)silane;
dimethylbis-6-(2,5-dimethyl-3-phenylcyclopentadienyl-[1,2-b]-tellurophene)silane;
dimethylbis-6-[2,5-dimethyl-3-(2-methylphenyl)cyclopentadienyl-[1,2-b]-tellurophene]silane;
dimethylbis-6-[2,5-dimethyl-3-(2,4,6-trimethylphenyl)cyclopentadienyl-[1,2-b]-tellurophene]silane;
dimethylbis-6-[2,5-dimethyl-3-mesitylenecyclopentadienyl-[1,2-b]-tellurophene]silane;
dimethylbis-6-(2,4,5-trimethyl-3-phenylcyclopentadienyl-[1,2-b]-tellurophene)silane;

dimethylbis-6-(2,5-diethyl-3-phenylcyclopentadienyl-[1,2-b]-tellurophene)silane;
dimethylbis-6-(2,5-diisopropyl-3-phenylcyclopentadienyl-[1,2-b]-tellurophene)silane;
dimethylbis-6-(2,5-diter-butyl-3-phenylcyclopentadienyl-[1,2-b]-tellurophene)silane;
dimethylbis-6-(2,5-ditrimethylsilyl-3-phenylcyclopentadienyl-[1,2-b]-tellurophene)silane;
dimethylbis-6-(3-methylcyclopentadienyl-[1,2-b]-tellurophene)silane;
dimethylbis-6-(3-isopropylcyclopentadienyl-[1,2-b]-tellurophene)silane;
dimethylbis-6-(3-phenylcyclopentadienyl-[1,2-b]-tellurophene)silane;
dimethylbis-6-(2,5-dimethyl-3-phenylcyclopentadienyl-[1,2-b]-tellurophene)silane;
dimethylbis-6-[2,5-dimethyl-3-(2-methylphenyl)cyclopentadienyl-[1,2-b]-tellurophene]silane;
dimethylbis-6-[2,5-dimethyl-3-(2,4,6-trimethylphenyl)cyclopentadienyl-[1,2-b]-tellurophene]silane;
dimethylbis-6-[2,5-dimethyl-3-mesitylenecyclopentadienyl-[1,2-b]-tellurophene]silane;
dimethylbis-6-(2,4,5-trimethyl-3-phenylcyclopentadienyl-[1,2-b]-tellurophene)silane;
dimethylbis-6-(2,5-diethyl-3-phenylcyclopentadienyl-[1,2-b]-tellurophene)silane;
dimethylbis-6-(2,5-diisopropyl-3-phenylcyclopentadienyl-[1,2-b]-tellurophene)silane;
dimethylbis-6-(2,5-diter-butyl-3-phenylcyclopentadienyl-[1,2-b]-tellurophene)silane;
dimethylsilyl-6-(2,5-dimethyl-3-phenylcyclopentadienyl-[1,2-b]-tellurophene)-1-(2-methyl-4-phenylindenyl)silane;
dimethylbis-6-(2,5-ditrimethylsilyl-3-phenylcyclopentadienyl-[1,2-b]-tellurophene)silane;
dimethylbis-6-(3-methylcyclopentadienyl-[1,2-b]-phosphole)silane;
dimethylbis-6-(3-isopropylcyclopentadienyl-[1,2-b]-phosphole)silane;
dimethylbis-6-(3-phenylcyclopentadienyl-[1,2-b]-phosphole)silane;
dimethylbis-6-(2,5-dimethyl-3-phenylcyclopentadienyl-[1,2-b]-phosphole)silane;
dimethylbis-6-[2,5-dimethyl-3-(2-methylphenyl)cyclopentadienyl-[1,2-b]-phosphole]silane;
dimethylbis-6-[2,5-dimethyl-3-(2,4,6-trimethylphenyl)cyclopentadienyl-[1,2-b]-phosphole]silane;
dimethylbis-6-[2,5-dimethyl-3-mesitylenecyclopentadienyl-[1,2-b]-phosphole]silane;
dimethylbis-6-(2,4,5-trimethyl-3-phenylcyclopentadienyl-[1,2-b]-phosphole)silane;
dimethylbis-6-(2,5-diethyl-3-phenylcyclopentadienyl-[1,2-b]-phosphole)silane;
dimethylbis-6-(2,5-diisopropyl-3-phenylcyclopentadienyl-[1,2-b]-phosphole)silane;
dimethylbis-6-(2,5-diter-butyl-3-phenylcyclopentadienyl-[1,2-b]-phosphole)silane;
dimethylbis-6-(2,5-ditrimethylsilyl-3-phenylcyclopentadienyl-[1,2-b]-phosphole)silane;
dimethylsilandiyl-6-(2,5-dimethyl-3-phenylcyclopentadienyl-[1,2-b]-thiophene)-1-(2-methyl-4-phenylindenyl)silane;
dimethylsilandiyl-6-(2,5-dimethyl-3-phenylcyclopentadienyl-[1,2-b]-phosphole)-1-(2-methyl-4-phenylindenyl)silane;
dimethylsilandiyl-6-(2,5-dimethyl-3-phenylcyclopentadienyl-[1,2-b]-tellurophene)-1-(2-methyl-4-phenylindenyl)silane.

Most preferably the ligands according to the present invention are dimethylbis-6-(2,5-dimethyl-3-phenylcyclopentadienyl-[1,2-b]-thiophene)silane;
dimethylbis-6-[2,5-dimethyl-3-(2'-methylphenyl)cyclopentadienyl-[1,2-b]-thiophene]silane;
dimethylbis-6-(3,5-dimethylcyclopentadienyl-[1,2-b]-thiophene)silane.

The aforementioned compounds of formula (V) are particularly useful as intermediate ligands for the preparation of the metallocene compounds of formula (I). According to a further aspect of the present invention there is provided a process for the preparation of a ligand of formula (V), wherein L, Y' and Z' are defined as described above, with the proviso that $R^2$ is a hydrogen and D is a carbon atom, comprising the following steps:

a) contacting a compound of general formula (IX):

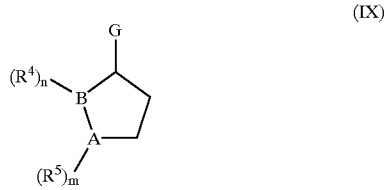

(IX)

wherein the double bonds can be in any of the allowed positions;

A, B, $R^4$, $R^5$, n and m have the meaning as defined above, G is a halogen atom, with an alkylation agent selected from $(R^3)_5MgQ$, $(R^3)_5M'$ being an alkali metal selected from sodium, potassium and lithium, or a metal selected from the group 10 to 12 from the Periodic Table of the Elements (new IUPAC version), Q being a halogen selected from chloride, bromide and iodide, in the presence of a coupling agent;

b) contacting a compound obtained under a) with a compound of general formula (X):

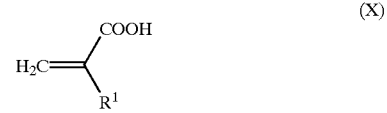

(X)

wherein $R^1$ has the same meaning as defined above;
In the presence of a ring-closure agent, to obtain the compound of the general formula (XI):

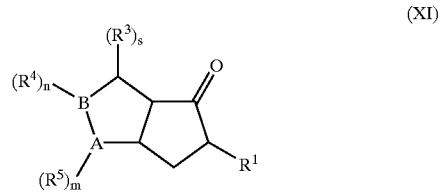

(XI)

c) conversion into the compound of formula (XII):

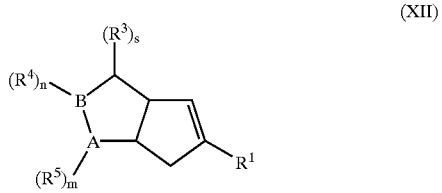

and when Z' is equal to Y', wherein A and B in Y' and Z' are the same or different from each other:

d1) treating the compound of formula (XII) with a base selected from hydroxides and hydrides of alkali- and earth-alkali metals, metallic sodium and potassium, and organometallic lithium salts, and subsequently contacting with a compound of formula $LQ_2$ (XIII), wherein L has the same meaning as defined above, and Q is a halogen, wherein the molar ratio between the compound of formulae (XII) and (XIII) is at least 2;

or when Z' is a compound of formula (VII):

d2) treating the compound of formula (XII) with a base as defined under d1), and subsequently contacting with a compound of formula Z'LQ (XIV), wherein L has the same meaning as defined above, and Q is a halogen;

or where Y' is equal to Z' and $R^2$ is defined as $R^7$:

treating the ligand of formula (V) with a base as defined under c1), wherein the molar ratio between the base and the compound of formula (V) is at least 2, and subsequent with a compound of formula $R^2Q$, Q being a halogen atom selected from chloride, iodide and bromide. Preferably in the process according to the present invention the ring-closing agent is selected from phosphorus pentoxide-methansulfonic acid (PPMA) and polyphosphoric acid (PPA).

In the process according to according to the present invention the compound of general formula (X) is selected from α,β-unsaturated acids. Most preferably methacrylic acid is used.

Preferably, in the process according to the present invention the compound of general formula (IX) is 1-methyl-3-bromo-thiophene.

In the process according to the present invention the conversion into the compound of formula (XII) preferably is carried out in the presence of a reduction agent and paratoulene sulfonic acid monohydrate.

In the process according to the present invention the reduction agent is preferably lithium aluminium hydride ($LiAlH_4$).

Non-limiting examples of compounds of formula $LQ_2$ (XIII) are dimethyldichlorosilane, diphenyldichlorosilane, dimethyldichlorogermanium, 2,2-dichloropropane and 1,2-dibromoethane.

Preferably, in the process according to the present invention the compound of formula $LQ_2$ (XIII) is dimethyldichlorosilane.

Non-limiting examples of compounds able to form the anionic compound of formula (XII) are hydroxides and hydrides of alkali- and earth-alkali metals, metallic sodium and potassium, and organometallic lithium salts. Preferably butyllithium is used.

Non-limiting examples of coupling agent used in step a) are Ni, Pd or Pt-based coupling agent. Coupling agents of this kind which are generally used are described in "Comprehensive organic synthesis", Eds. B. M. Trost and I. Fleming, Pergamon, Oxford (1991), Vol. 3, Part 1.6, p.241. Preferably bis(diphenylphosphino)propane)]dichloronickel (II) (Ni(dPPP)) is used.

The synthesis of the above bridged ligands is preferably carried out by adding a solution of an organic lithium compound in an apolar solvent to a solution of the compound (XII) in an aprotic polar solvent. The thus obtained solution containing the compound (XII) in the anionic form is then added to a solution of the compound of formula $LQ_2$ (XIII) in an aprotic polar solvent. The bridged ligand can be finally separated by conventional general known procedures.

Not limitative examples of aprotic polar solvents which can be used in the above process are tetrahydrofurane, dimethoxyethane, diethylether, toluene and dichloromethane. Not limitative examples of apolar solvents suitable for the above process are pentane, hexane and benzene.

During the whole process, the temperature is preferably kept between −180° C. and 80° C., and more preferably between −20° C. and 40° C.

A still further aspect of the present invention is a process for the preparation of the metallocene compounds of formula (I), obtainable by contacting a ligand of formula (IV) as described above, with a compound capable of forming a corresponding dianionic compound thereof and thereafter with a compound of formula $MX_{p+2}$, wherein M, X and p have the meanings as defined above.

The compound able to form said dianion is selected from the group consisting of hydroxides and hydrides of alkali- and earth-alkali metals, metallic sodium and potassium, and organometallic lithium salts, and preferably said anion is n-butyllithium.

Non-limiting examples of compounds of formula $MX_{p+2}$ are titanium tetrachloride, zirconium tetrachloride and hafnium tetrachloride.

More specifically, said bridged ligands are dissolved in an aprotic polar solvent and to the obtained solution is added a solution of an organic lithium compound in an apolar solvent. The thus obtained anionic form is separated, dissolved in an aprotic polar solvent and thereafter added to a suspension of the compound $MX_{p+2}$ in an aprotic polar solvent. At the end of the reaction, the solid product obtained is separated from the reaction mixture by techniques commonly used in the state of the art. Non limiting examples of aprotic polar solvents suitable for the above reported processes are tetrahydrofurane, dimethoxyethane, diethylether, toluene and dichloromethane. Non limiting examples of apolar solvents suitable for the above process are pentane, hexane and benzene.

During the whole process, the temperature is preferably kept between −180° C. and 80° C., and more preferably between −20° C. and 40° C.

When at least one X substituent in the metallocene compound of formula (I) is different from halogen, it is necessary to substitute at least one substituent X in the obtained metallocene with at least another substituent different from halogen. Such a substitution reaction is carried out by methods known in the state of the art. For example, when the substituents X are alkyl groups, the metallocenes can be reacted with alkylmagnesium halides (Grignard reagents) or with lithiumalkyl compounds.

During the whole process, the temperature is preferably kept between −180° C. and 80° C., and more preferably between −20° C. and 40° C.

The heterocyclic metallocene compounds of the present invention can conveniently be used as catalyst components for the polymerization of olefins.

Thus, according to a still further aspect of the present invention there is provided a catalyst for the polymerization of olefins, obtainable by contacting:

a metallocene compound of formula (I), and an alumoxane and/or a compound capable of forming an alkyl metallocene cation.

The alumoxane used as component (B) can be obtained by reacting water with an organo-aluminium compound of formula $AlR^{18}_3$ or $Al_2R^{18}_6$, where $R^{18}$ substituents, same or different, are hydrogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms some $R^{18}$ substituents can be halogen atoms. In this reaction the molar ratio of Al/water is comprised between 1:1 and 100:1.

The molar ratio between aluminium and the metal of the metallocene is comprised between about 10:1 and about 20000:1, and preferably between about 100:1 and about 5000:1.

The alumoxanes used in the catalyst according to the invention are considered to be linear, branched or cyclic compounds containing at least one group of the type:

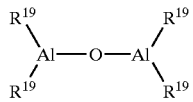

wherein the $R^{19}$ substituents, same or different, are hydrogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms, or are a —O—Al($R^{19}$)$_2$ group and, if appropriate, some $R^{19}$ substituents can be halogen atoms.

In particular, alumoxanes of the formula:

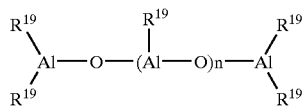

can be used in the case of linear compounds, wherein n is 0 or an integer from 1 to 40 and the $R^{19}$ substituents are defined as above, or alumoxanes of the formula:

can be used in the case of cyclic compounds, wherein n is an integer from 2 to 40 and the $R^6$ substituents are defined as above.

Examples of alumoxanes suitable for use according to the present invention are methylalumoxane (MAO), tetra-(isobutyl)alumoxane (TIBAO), tetra-(2,4,4-trimethylpentyl) alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 in which the alkyl groups have specific branched patterns.

Non-limiting examples of aluminium compounds according to said PCT application are: tris(2,3,3-trimethyl-butyl) aluminium, tris(2,3-dimethyl-hexyl)aluminium, tris(2,3-dimethyl-butyl)aluminium, tris(2,3-dimethyl-pentyl) aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl) aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl) aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl) aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl) aluminium, tris(2,3-dimethyl-3-phenyl-butyl)aluminium, as well as the corresponding compounds wherein one of the hydrocarbyl groups is replaced by an hydrogen atom, and those wherein one or two of the hydrocarbyl groups are replaced by an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

In the catalyst used in the process according to the invention for the preparation of polyolefins, both the heterocyclic metallocene compound of the formula (I) and the alumoxane can be present as the product of the reaction with an organometallic aluminium compound of the formula $AlR^{18}_3$ or $Al_2R^{18}_6$, in which the $R^{18}$ substituents, same or different, are hydrogen atoms, halogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms.

Non-limiting examples of aluminium compounds of the formula $AlR^{18}_3$ or $Al_2R^{18}_6$ are: Al(Me)$_3$, Al(Et)$_3$, AlH(Et)$_2$, Al(iBu)$_3$, Al(iHex)$_3$, Al(iOct)$_3$, Al(C$_6$H$_5$)$_3$, Al(CH$_2$C$_6$H$_5$)$_3$, Al(CH$_2$CMe$_3$)$_3$, Al(CH$_2$SiMe$_3$)$_3$, Al(Me)$_2$iBu, Al(Me)$_2$Et, AlMe(Et)$_2$, AlMe(iBu)$_2$, Al(Me)$_2$iBu, Al(Me)$_2$Cl, Al(Et)$_2$Cl, AlEtCl$_2$, Al$_2$(Et)$_3$Cl$_3$, wherein Me=methyl, Et=ethyl, iBu= isobutyl, iHex=isohexyl, iOct=2,4,4-trimethyl-pentyl.

Among the aforementioned aluminium compounds, trimethylaluminium (TMA), triisobutylaluminium (TIBAL) and tris(2,4,4-trimethyl-pentyl)aluminium (TIOA) are preferred.

Non limitative examples of compounds able to form a metallocene alkyl cation are compounds of formula T$^+$D$^-$, wherein T$^+$ is a Broensted acid, able to give a proton and to react irreversibly with a substituent L of the metallocene of formula (I), and D$^-$ is a compatible anion, which does not coordinate, which is able to stabilize the active catalytic species which originates from the reaction of the two compounds and which is sufficiently labile to be able to be removed from an olefinic substrate. Preferably, the anion D$^-$ comprises one or more boron atoms. More preferably, the anion D$^-$ is an anion of the formula BAr$^{(-)}_4$, wherein substituents Ar, the same or different from each other, are aryl radicals such as phenyl, pentafluorophenyl, bis (trifluoromethyl)phenyl. Particularly preferred is the tetrakis-pentafluorophenyl borate. Furthermore, compounds of formula BAr$_3$ can be suitably used.

The catalysts used in the process of the present invention can be also used on inert supports. This is obtained by depositing the metallocene (A), or the product of the reaction of the same with the component (B), or the component (B) and thereafter the metallocene (A), on supports such as for example silica, alumina, styrene-divinylbenzene copolymers, polyethylene or polypropylene.

The solid compound so obtained, in combination with further addition of the alkyl aluminium compound as such or pre-reacted with water, is usefully employed in gas phase polymerisation.

Catalysts of the present invention are useful in the homo- and copolymerization reaction of olefins.

Therefore, a still further object of the present invention is a process for the polymerization of olefins comprising the polymerization reaction of at least an olefinic monomer in the presence of a catalyst as above described.

The catalysts of the present invention can be used in the homo-polymerisation reaction of olefins, such as ethylene for the preparation of HDPE, or of alpha-olefins, such as propylene and 1-butene.

Particular interesting results are achieved in the polymerisation of propylene carried out in the presence of the above-described catalyst containing the metallocene of the present invention.

It has been found that when the polymerization of propylene is carried out in the presence of the metallocene compounds of the present invention, the molecular weight of the obtained propylene polymers are unexpectedly high. The intrinsic viscosity (I.V.) of the obtained polypropylene is generally higher than 1 dL/g and can reach values as high as 5 dL/g or even higher.

The obtained propylene polymers are characterized by high isotacticity values. Thus, the amount of sequences mrrn (in mol %) is extremely low. In generally the amount of sequences mrrm (in mol %) is lower than 1, preferably lower than 0.5.

When the polymerization of propylene is carried out in the presence of the metallocene compounds of the present invention the melting point of the obtained polypropylene is considerably high. In generally the melting point of the obtained polypropylene is higher than 145° C. and can reach values of 160° C. or even higher.

A still further advantageous characteristic of the metallocenes of the invention is that the use of a small amount of hydrogen, besides regulating the molecular weight, entails a considerable increase of the polymerization activities.

Another interesting use of the catalysts according to the present invention is in the copolymerization of ethylene with higher olefins. In particular, the catalysts of the invention can be used for the preparation of LLDPE.

Suitable olefins to be used as comonomers comprise α-olefins of the formula $CH_2=CHR^{20}$, wherein $R^{20}$ is an alkyl radical having from 1 to 10 carbon atoms or an aryl radical having from 6 to 20 carbon atoms, and cycloolefins. Examples of these olefins are propylene, 1-butene, 1-pentene, 4-methyl-1-pentene, 1-hexene, 1-octene, 1-decene, 1-dodecene, 1-tetradecene, 1-esadecene, 1-octadecene, 1-eicosene, allylcyclohexene, cyclopentene, styrene, cyclohexene, norbornene and 4,6-dimethyl-1-heptene.

The copolymers may also contain small proportions of units deriving from polyenes, in particular from straight or cyclic, conjugated or non conjugated dienes, such as 1,4-hexadiene, isoprene, 1,3-butadiene, 1,5-hexadiene and 1,6-heptadiene.

The units deriving from α-olefins of formula $CH_2=CHR^{20}$, $R^{20}$ is an alkyl radical having from 1 to 10 carbon atoms or an aryl radical having from 6 to 20 carbon atoms, from cycloolefins and/or from polienes are present in the copolymers preferably in amounts ranging from 1% to 20% by mole.

The saturated elastomeric copolymers can contain ethylene units and α-olefins and/or non conjugated diolefins able to cyclopolymerise. The unsaturated elastomeric copolymers can contain, together with the units deriving from the polymerisation of ethylene and α-olefins, also small proportions of unsaturated units deriving from the copolymerization of one or more polyenes. The content of unsaturated units is preferably comprised between 0 and 5% by weight.

Non limitative examples of suitable α-olefins comprise propylene, 1-butene and 4-methyl-1-pentene. Suitable non conjugated diolefins able to cyclopolymerise comprise 1,5-hexadiene, 1,6-heptadiene and 2-methyl-1,5-hexadiene.

Non limitative examples of suitable polyenes are:
(i) polyenes able to give unsaturated units, such as:
linear, non-conjugated dienes, such as 1,4-hexadiene trans, 1,4-hexadiene cis, 6-methyl-1,5-heptadiene, 3,7-dimethyl-1,6-octadiene and 11-methyl-1,10-dodecadiene;
bicyclic diolefins, such as 4,5,8,9-tetrahydroindene and 6 and 7-methyl-4,5,8,9-tetrahydroindene;
alkenyl or alkyliden norbornenes, such as 5-ethyliden-2-norbornene, 5-isopropyliden-2-norbornene and exo-5-isopropenyl-2-norbornene;
polycyclic diolefins, such as dicyclopentadiene, tricyclo-$[6.2.1.0^{2.7}]^{4,9}$-undecadiene and the 4-methyl derivative thereof;
(ii) non-conjugated diolefins able to cyclopolymerise, such as 1.5-hexadiene, 1,6-heptadiene and 2-methyl-1,5-hexadiene;
(iii) conjugated dienes, such as butadiene and isoprene.

A further interesting use of the catalysts according to the present invention is for the preparation of cycloolefin polymers. Monocyclic and polycyclic olefin monomers can be either homopolymerised or copolymerised, also with linear olefin monomers. Polymerisation processes according to the present invention can be carried out in gaseous phase or in liquid phase, optionally in the presence of an inert hydrocarbon solvent either aromatic (such as toluene), or aliphatic (such as propane, hexane, heptane, isobutane and cyclohexane).

The polymerisation temperature generally ranges from about 0° C. to about 250° C. In particular, in the processes for the polymerization of propylene, it is generally comprised between 20° C. and 150° C., preferably between 40° C. and 90° C.

The polymerization pressure is ranging from 0,5 to 100 bar, preferably from 2 to 50 bar, and more preferably from 4 to 30 bar.

The molecular weight of the polymers can be also varied merely by varying the polymerization temperature, the type or the concentration of the catalytic components or by using molecular weight regulators such as, for example, hydrogen.

The molecular weight distribution can be varied by using mixtures of different metallocenes, or carrying out the polymerization in several steps at different polymerization temperatures and/or different concentrations of the molecular weight regulator.

The polymerization yields depend on the purity of the metallocene component of the catalyst. Therefore, in order to increase the yields of polymerization, metallocenes are generally used after a purification treatment.

The components of the catalyst can be brought into contact before the polymerization. The pre-contact concentrations are generally between 1 and $10^{-8}$ mol/l for the metallocene component (A), while they are generally between 10 and $10^{-8}$ mol/l for the component (B). The pre-contact is generally effected in the presence of a hydrocarbon solvent and, if appropriate, of small quantities of monomer. The pre-contact time is generally comprised between 1 minute and 24 hours.

FIG. 1 reports a computer generated diagram of the metallocene compound prepared in Example 1 based on X-ray crystallography data.

Figure 2:
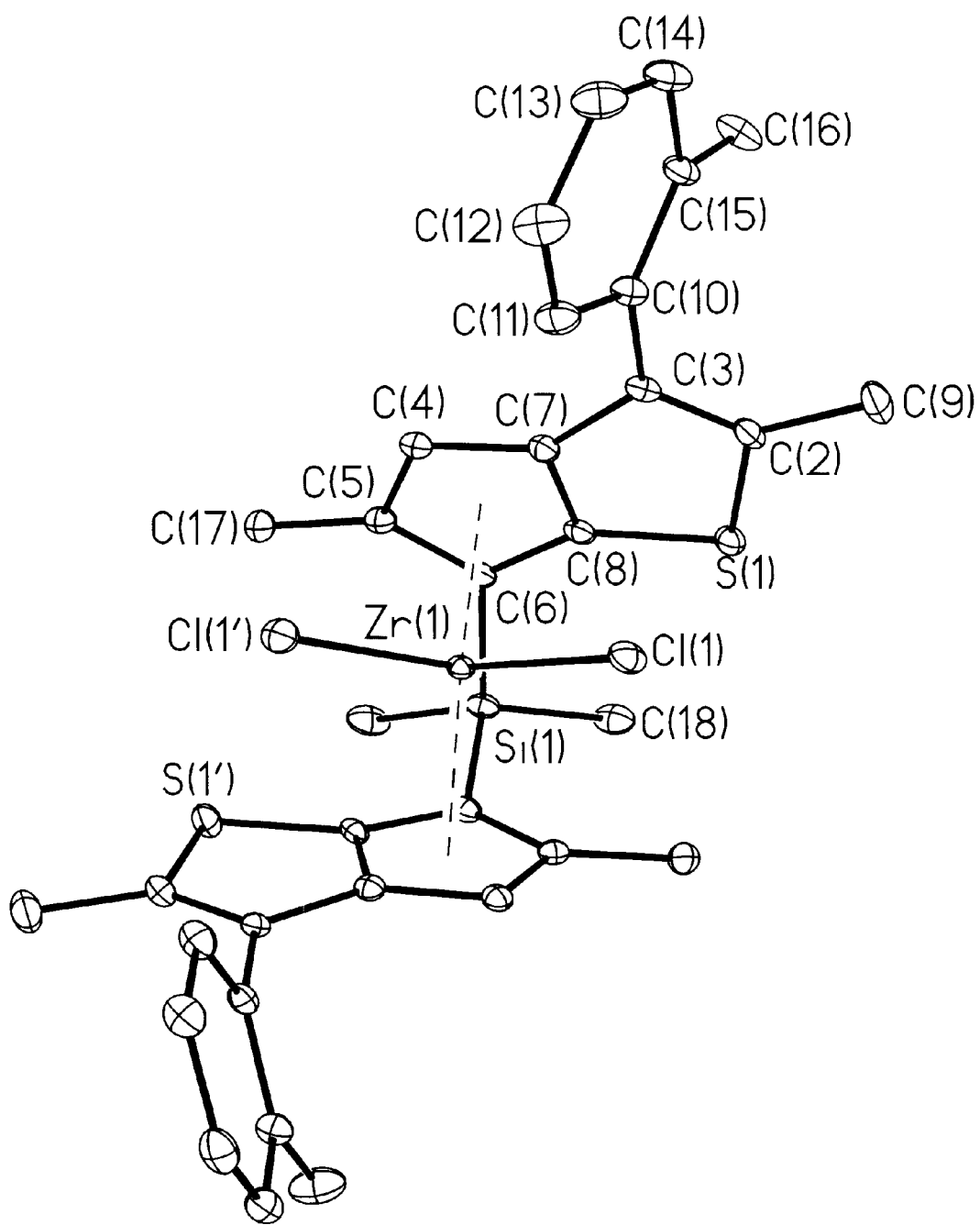

FIG. 2 reports a computer generated diagram of the metallocene compound prepared in Example 2 based on X-ray crystallography data.

The following examples are given to illustrate and not to limit the invention.

Experimental Part

General Materials and Procedures

All syntheses were performed under a dinitrogen atmosphere in pre-dried glassware unless stated otherwise. Solvents for air-sensitive compounds were purified as follows: THF, ether, and toluene were distilled from sodium/benzophenone, pentane was distilled from sodium/benzophenone/tri-glyme, dichloromethane was distilled from $CaH_2$ and stored over 4A sieves. Methylalumoxane (10 wt % toluene sol.) was purchased from Witco Corp.

MS. Mass spectra of organic intermediates were measured with an HP 6890 series GC equipped with a 5973 mass selective detector.

IV. Intrinsic viscosities were determined in decalin at 135° C.

NMR. Proton spectra were run on a Varian Unity-300 NMR spectrometer at 300 MHz. For polymer NMR analyses, the solution $^{13}$C-NMR spectra were run at 75.4 MHz on a Varian UNITY-300 NMR spectrometer. The samples were run as 10% (w/v) solutions in orthodichlorobenzene-$d_4$ at 130° C. Chemical shifts are referenced to TMS using a secondary reference, the $CH_3$ methyl peak of polypropylene at 21.8 ppm. 5000 transients were accumulated for each spectrum with a 10-second delay between pulses. Decoupling was always on during acquisition so the nuclear Overhauser enhancement was present.

DSC. In this method measurement of transition temperature and enthalpy of melting and crystallization of plastic materials is accomplished using a power-compensation mode Perkin Elmer (PE) DSC7 (Serial #134302) and PE PYRIS (revision 3.03) software. A PE Intercooler II (Model FC100PEA Serial #FC079441) is used for cooling. The instrument is calibrated against certified (1) indium lot #M16-01, 0138 Batch El with Teim=156.60° C.; Hf=28.71 J/g and (2) tin lot #LGC2609 0164 Batch 001-Teim 231.88° C.; Hf=60.46 J/g. Temperature and energy calibration is checked daily and repeatability is better than 2%. The dynamic heating/cooling rate is 20° C./min. The purge gas is nitrogen flowing at 20±2 cc/min. A three ramp (heat-cool-reheat) procedure is employed. The upper and lower tem perature limits are 25 and 235° C. respectively. The isothermal hold time between ramps is 3 minutes.

Preparation of the Metallocenes

EXAMPLE 1

Synthesis of dimethylsilandiylbis-6-(2,5-dimethyl-3-phenylcyclopentadienyl-[1,2-b]-thiophene)zirconium dichloride-$SiMe_2(Me_2PhCpThiophen)ZrCl_2$ (see FIG. 1)

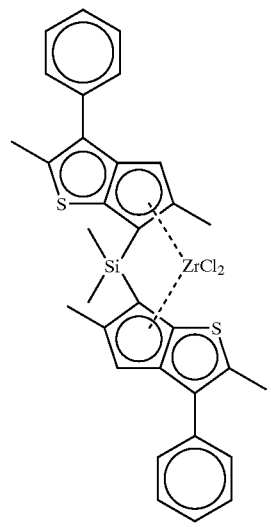

Synthesis of 2-methyl-3-bromothiophene

In situ synthesis of LDA: In a 1l 3-neck flask equipped with stirbar and 125 ml pressure equalized addition funnel was added 62.0 g (610 mmol, 88 ml) diisopropylamine dissolved in 150 ml THF. Dropwise, a 2.5M solution of butyllithium in hexane (610 mmol, 210 ml) was added while maintaining the temperature at 0° C. After addition was complete, stirring continued for an additional 30 m.

Synthesis of 2-methyl-3-bromothiophene

The flask containing LDA (prepared above) was cooled to −78° C. then 100 g (610 mmol) 3-bromothiophene dissolved in 60 ml THF was added dropwise. After addition was complete, the solution was warmed to 0° C. (ice bath), then stirred an additional 30 m. The temperature of the reaction slurry was then lowered to −78° C., then a solution containing 86.5 g (610 mmol) iodomethane dissolved in 40 ml THF was added in one portion. The reaction mixture was stirred an additional 30 m. at −78° C., then warmed to room temperature and stirred an additional 1 h. The organic layer was collected with diethylether, washed with water, dried over magnesium sulfate, filtered, then solvents were removed in vacuo. A light orange oil (89.8 g, 90.7% by GC) was recovered. Yield: 74.8%.

Synthesis of 2-methyl-3-phenylthiophene

In a 1 l 3neck round bottled flask equipped with stirbar, condenser, and 125 ml pressure equalized addition funnel was added 1 g bis(diphenylphosphino)propane)]

dichloronickel(II) (dPPP) in 200 ml diethylether, then 89.8 g (460 mmol) 3-bromo-2-methylthiophene. Dropwise, a 3M solution of phenylmagnesium bromide in diethyl ether (456 mmol, 152 ml) was added. After addition was complete, the reaction flask was stirred an additional 1 h., then quenched with water. The organic fraction was collected with dichloromethane, washed with water, dried over magnesium sulfate, then the solvent removed in vacuo. A dark orange oil. (77.13 g, 87.2% by GC) was recovered. Yield: 84.7%. The title compound was analysed by mass and $^1$H-NMR spectroscopy.

Synthesis of 2-methyl-3-phenyl-5,6-dihydrocyclopenta[1,2-b]thiophen-4-one

In a 2 l 5 neck round bottled flask equipped with nitrogen inlet, 250 ml pressure equalized addition funnel, reflux condenser, thermometer, and mechanical stir was added 1 Kg polyphosphoric acid (Aldrich, 84%). The temperature was raised to 100° C., then 180 g-phosphorus pentoxide was added and the temperature was raised to 130° C. Stirring was continued until all the phosphorus pentoxide had dissolved then the flask and contents were cooled to 80° C. A solution containing 79.2 g (455 mmol) 3-phenyl-2-methylthiophene and 40.1 g (465 mmol) methacrylic acid (Aldrich) dissolved in 100 ml dichloromethane was added slowly. Stirring continued with refluxing dichloromethane for 7 h, during which time an additional 130.8 g (1.52M) methacrylic acid in 250 ml dichloromethane was added (in portions, every 1.5 h). The contents of the flask were poured on to ice, the organic layer was collected with 20% dichloromethane in hexane, washed with water, neutralized with a saturated solution of sodium bicarbonate, then again washed with water. The organic fraction was dried over magnesium sulfate, filtered, then the solvents were removed in vacuo. Yield: 71.4 g (65%) (89.32 g dark orange oil, 80% by GC: used in subsequent steps without further purification). The title compound was analysed by $^1$H-NMR spectroscopy.

Synthesis of 2,5-dimethyl-3-phenyl-5,6-dihydrocyclopenthiophene-5-ol

In a 2 l round bottled flask with stirbar and 500 ml addition funnel was added 202 g [(at 82%=680 mmol)] 2,5-dimethyl-3-phenyl-4,5-dihydrocyclopentathiophen-4-one dissolved in 300 ml THF. The solution was cooled to 0° C., then a 1.0M solution of lithium aluminum hydride in diethylether (300 mmol, 300 ml) was added dropwise. After addition was complete, the temperature of the reaction flask was raised to room temperature, then stirred an additional 2 h. The reaction was quenched with water, the organic layer was collected with diethylether, washed with water, dried over magnesium sulfate, filtered, and then the solvents were removed in vacuo. Yield: 123.1 g yellow solid. An additional 16 g of material was recovered by repeated washing of the lithium-prill. (78.5% by GC; 75% overall yield).

Synthesis of 2,5-dimethyl-3-phenylcyclopenta[1,2-b]thiophene

In a 500 ml round bottled flask with stirbar and reflux condenser was placed 28 g, 114.3 mmol) 2,5-dimethyl-3-phenyl-5,6-dihydrocyclopenthiophene-5-ol dissolved in 100 ml toluene. A 1 g portion of para-toulene sulfonic acid monohydrate was added, the mixture was refluxed for 30 min. The reaction mixture was quenched with water, the organic layer was washed with water, bicarbonate, then water, dried over magnesium sulfate, filtered, then the solvents were removed in vacuo. A dark red oil (26.6 g, 87% by GC) was recovered. Yield: 90%. The desired compound was analyzed by mass spectrometry.

Synthesis of bis[6,6'-(2,5-dimethyl-3-phenylhydrocyclopenta[1,2-b]thiophene)] dimethylsilane In a 500 ml round bottled flask with sidearm, stirbar, and 60 ml pressure equalized addition funnel was added 22.6 g (100 mmol) 2,5-dimethyl-3-phenylhydrocyclopenta[1,2-b]thiophene) dissolved in 80 ml THF. Dropwise, a 2.5M solution of n-butyllithium in hexane (100 mmol, 40 ml) was added at room temperature. The contents of the flask were stirred for an additional 5 h. In a separate 500 ml round bottled flask with 250 ml additional funnel was added 6.45 g (50 mmol) dimethyldichlorosilane dissolved in 40 ml THF. The flask temperature was lowered to −78° C., then the THF solution containing anion prepared above was added dropwise. After addition was complete, the flask and contents were allowed to warm to room temperature then stirred an additional 6 h. The reaction mixture was poured onto water, then the organic fraction was collected with dichloromethane, dried over magnesium sulfate, and concentrated in vacuo. The solids were recrystallized from diethylether and collected on a medium frit filter. The white solids collected in this fashion were dried in vacuo: Yield: 11.33 g white free flowing powder, 99% by GC (Yield: 45%). The title compound was analysed by $^1$H-NMR spectroscopy.

Synthesis of dimethylsilandiylbis-6-(2,5-dimethyl-3-phenylcyclopentadienyl-[1,2-b]-thiophene)zirconium dichloride In a 250 ml round bottled flask with sidearm and stirbar was placed 1.82 g (3.6 mmol) dimethylsilandiylbis[6,6'-(2,5-dimethyl-3-phenylhydrocyclopenta[1,2-b]thiophene)] slurried in 100 ml of diethylether. Dropwise, a 2.5M solution of n-butyllithium in hexane (2.9 ml, 7.2 mmol) was added at room temperature. Stirring was continued for 5 h., then 0.83 g (3.6 mmol) zirconium tetrachloride was slowly added. The reaction flask was stirred an additional 3 h, then the solution was filtered. The solids collected in this fashion were washed with fresh diethyl ether, then the solvents were removed in vacuo leaving 770 mg of a 3:5 rac/meso mixture. The solids remaining on the filter were then slurried in dichloromethane, filtered, and the solvents were removed from the solution in vacuo. 350 mg pure-rac isomer was recovered. Yield: 1.12 g, 47%. The title compound was analysed by $^1$H-NMR spectroscopy.

EXAMPLE 2

Synthesis of dimethylsilandiylbis-6-[2,5-dimethyl-3-(2'-methyl-phenyl)cyclopentadienyl-[1,2-b]-thiophene]zirconium dichloride-SiMe$_2$[Me$_2$(MePh) CpThiophen]ZrCl$_2$ (see FIG. 2)

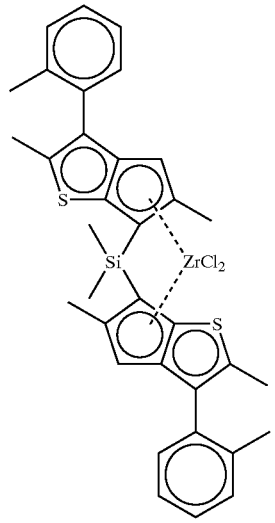

Synthesis of 2-Me-3-bromothiophene

A solution of 3-bromothiophene (17.4 g, 0.107 mol) in 10 mL of THF was added dropwise to lithium diisopropylamide (12.5 g, 0.110 mol) in THF (75 mL) at −78° C. After completing the addition, the reaction mixture was slowly warmed to 0° C. and stirred for 0.5 h. The dark solution was cooled to −78° C. and treated with iodomethane (2.28 g, 0.110 mol). The temperature was raised to −10° C. and stirring continued for 15 minutes. Water (100 mL) was added slowly and most of the THF was evaporated on a rotoevaporator. The product was extracted with ether (2×100 mL) and dried (MgSO$_4$). Rotoevaporation of the solvent yielded 12 g of crude product (68%). The title compound was analysed by $^1$H-NMR spectroscopy.

Synthesis of 2-Me-3-(2-MePh)-thiophene

An ether solution of o-tolylmagnesium bromide (350 mL of a 2.0 M sol., 0.7 mol) was added slowly to a mixture of 2-methyl-3-bromothiophene (123 g, 0.7 mol) and 1.2 g of Ni(dppp)Cl$_2$ in 50 mL of ether. After stirring overnight, water (200 mL) was added cautiously and the organic layer was separated, washed with brine solution (100 mL), and dried (MgSO$_4$). Rotoevaporation of solvents yielded 136 g of crude product (72%). The title compound was analysed by $^1$H-NMR and mass spectroscopy.

Synthesis of 2,5-Me$_2$-3-(2-MePh)-5,6-dihydrocyclopenta[1,2-b]thiophene-4-one A solution of 2-Me-3-(2-MePh)-thiophene (80 g, 0.43mol) and methacrylic acid (44 g, 0.51 mol) in 100 mL of dichloromethane was added dropwise to 1000 g of 87% PPA at 80° C. and stirred for 5 h. The dark red mixture was poured onto crushed ice (1000 g) and stirred until the PPA was completely decomposed. The product was extracted with 30% (v/v) dichloromethane in hexane (2×400 mL). The combined organic fractions were washed with a saturated aqueous solution of NaHCO$_3$ and dried (MgSO$_4$). Solvents were removed on a rotoevaporator leaving 74 g of crude product (68%). The product was used without further purification. The title compound was analysed by $^1$H-NMR, $^{13}$C-NMR and mass spectroscopy.

Synthesis of 2,5-Me$_2$-3-(2-MePh)-6-hydrocyclopenta[1,2-b]thiophene

A solution of 2,5-Me$_2$-3-(2-MePh)-5,6-dihydrocyclopenta[1,2-b]thiophene-4-one (74 g, 0.286 mol) in 200 mL of THF was treated with 145 mL of LiAlH$_4$ in THF (1.0 M sol., 0.145 mol) at 0° C. After stirring at room temperature for 3 h, water was added cautiously (50 mL) and the resulting slurry was filtered. THF was evaporated from the filtrate and the solid filter cake was washed with dichloromethane (3×150 mL) into the filtrate residue. The dichloromethane solution was washed with water (50 mL), dried (MgSO$_4$), and evaporated to a brown liquid (67.2 g). The product was re-dissolved in 250 mL of toluene and stirred with 2.0 g of p-toluene sulfonic acid at 70° C. for 1.5 h. After cooling, the toluene solution was washed with water (50 mL), NaHCO$_3$ solution (50 mL), brine solution (50 mL), and dried (MgSO$_4$). Solvents were removed on a rotoevaporator leaving a dark oil. Distillation (120° C., ~0.05 torr) gave 47 g of product as a light yellow liquid (68 The title compound was analysed by $^1$H-NMR, $^{13}$C-NMR and mass spectroscopy.

Synthesis of Lithium salt of 2,5-Me$_2$-3-(2-MePh)-6-hydrocyclopenta[1,2-b]thiophene A solution of 2,5-Me$_2$-3-(2-MePh)-6-hydrocyclopenta[1,2-b]thiophene (20 g, 83.3 mmol) in 150 mL of ether was treated with 34 mL of n-butyllithium in hexanes (2.5 M sol., 85 mmol) and stirred at room temperature for 2.5 h. Pentane (150 mL) was added and the precipitated lithium salt was collected on a closed filter funnel, washed with pentane, and dried in vacuo (15 g of yellow powder The title compound was analysed by $^1$H-NMR and $^{13}$C-NMR spectroscopy.

Synthesis of 6-(Me$_2$SiCl)-2,5-Me$_2$-3-(2MePh)-6-hydrocyclopenta[1,2-b]thiophene A solution of the lithium salt of 2,5-Me$_2$-3-(2-MePh)-6-hydrocyclopenta[1,2-b]thiophene (7.3 g, ca. 30 mmol) in 75 mL of ether was cooled to −78° C. and treated with dichlorodimethylsilane (5.8 g, 45 mmol). The reaction mixture was warmed to room temperature, stirred overnight, and filtered through a closed frit. Volitiles were removed from the filtrate in vacuo (50° C., 0.1 torr) leaving the product as a light yellow oil (8.4 g, 25.2 mmol). The title compound was analysed by $^1$H-NMR spectroscopy.

Synthesis of 6,6'-(Me$_2$Si)-{2,5-Me$_2$-3-(2MePh)-6-hydrocyclopenta[1,2-b]thiophene}$_2$ A solution of 2,5-Me$_2$-3-(2-MePh)-6-hydrocyclopenta[1,2-b]thiophene (36.9 g, 0.154 mol) in 150 mL of THF was cooled to −78° C. and treated with 62 mL of n-butyllithium in hexanes (2.5 M sol., 0.155 mol). After stirring 16 h at room temperature the solution was added dropwise to a solution of dichlorodimethylsilane (9.94 g, 0.077 mol) in 70 mL of THF stirring at −78° C. The reaction mixture was slowly warmed to room temperature and stirred for 2 days. A saturated aqueous solution of NH$_4$Cl was added slowly (10 mL) and solvents were removed on a rotoevaporator. The residue was partitioned with ether (500 mL) and water (150 mL). The water layer was separated, re-extracted with fresh ether (100 mL), and the combined ether fractions were dried (MgSO$_4$). Evaporation of solvent yielded 41 g of an off-white solid (91% purity by GC). The crude product was chromatographed on silica (5% CH$_2$CL$_2$/hexane) in 2 runs. For one chromatographic run, 18.7 g of crude product, yielded 13.3 g of pure product (71%). The title compound was analysed by mass spectroscopy.

Synthesis of the dilithio salt of dimethylsilandiylbis-6-[2,5-dimethyl-3-(2'-methyl-phenyl)cyclopentadienyl-[1,2-b]-thiophene], SiMe$_2$[Me$_2$(MePh)CpThiophen]

6,6'-(Me$_2$Si)-{2,5-Me$_2$-3-(2MePh)-6-hydrocyclopenta[1,2-b]thiophene}$_2$ (2.9 g, 5.4 mmol) was dissolved in 50 mL of ether, cooled to −78° C., and treated with 4.8 mL of n-butyllithium in hexanes (2.5 M sol., 12 mmol). After stirring overnight at room temperature, the solvents were removed in vacuo leaving the product as a yellow-orange solid. The title compound was analysed by $^1$H-NMR spectroscopy.

Synthesis of dimethylsilandiylbis-6-[2,5-dimethyl-3-(2'-methyl-phenyl)cyclopentadienyl-[1,2-b]-thiophene]zirconium dichloride, SiMe$_2$[Me$_2$(MePh) CpThiophen]ZrCl$_2$ 6,6'-(Me$_2$Si)-{2,5-Me$_2$-3-(2MePh)-6-hydrocyclopenta[1,2-b]thiophene}$_2$ (27.6 g, 51.5 mmol) was dissolved in 200 mL of ether, cooled to −78° C., and treated with 42 mL of n-butyllithium in hexanes (2.5 M sol., 105 mmol). After stirring overnight at room temperature, solvents were removed in vacuo and pentane (150 mL) was added. The yellow slurry was cooled to −78° C. and treated with ZrCl$_4$ (11.7 g, 50.2 mmol). The reaction mixture was warmed to room temperature, stirred for 18 h, and filtered through a closed frit. The yellow solids were washed with pentane (ca. 60 mL) and dried under vacuum giving 33.8 g of crude product. The crude product was stirred in ca. 400 mL of dichloromethane at room temperature and filtered through dry celite. Solvent was evaporated from the filtrate under reduced pressure leaving 27.9 g of Me$_2$Si((2,5-Me$_2$-3-(o-Tolyl)-cyclopenteno[b]thiophene)$_2$ZrCl$_2$ as a 50/50 rac/meso mixture (78.5% yield The title compound was analysed by $^1$H-NMRspectroscopy.

EXAMPLE 3

Synthesis of dimethylsilandiylbis-6-[3,5-dimethylcyclopentadienyl-[1,2-b]-thiophene] zirconium dichloride-SiMe$_2$(Me$_2$CpThiophen)ZrCl$_2$

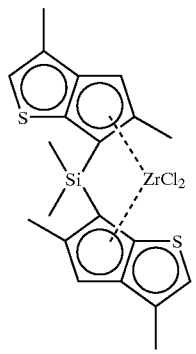

Synthesis of 2,5-dimethyl-6-hydrocyclopenta[1,2-b] thiophen-4-one

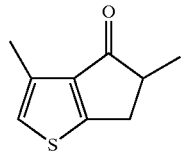

To a flask containing 950 g of 84% polyphoshopric acid (Aldrich) was added 180 g of P$_2$O$_5$. The slurry was heated to 140° C. for 4 h (until al P$_2$O$_5$ had dissolved), then cooled to 70° C. Dropwise, a solution containing 100 g (1.01 mol) 3-methylthiophene, 86 g (1 mol) methacrylic acid, and 60 ml dichioromethane was added. The mixture was refluxed for 2 h then the solution was poured onto ice. The organic layer was collected with a 30% dichloromethane/hexane solution which was washed with water, saturated bicarbonate solution, water, then dried over magnesium sulfate, filtered, then the solvents were removed in vacuo. 143 g of dark brown oil was recovered. The oil was distilled at 78° C. at 500 microns; 10.2 g of pale yellow oil was recovered (yield, 6.1%). The title compound was analysed by means of $^1$H-NMR spectroscopy.

Synthesis of 2,5-dimethyl-3-sulfonohydrazide-6-hydrocyclopenta[1,2-b]thiophene

To a flask containing 9.5 g (57 mmol) 3,5-dimethyl-5,6-dihydrocyclopenta[1,2-b]thiophen-4-one dissolved in 100 ml ethanol was added 10.6 g (57 mmol) para-toluenesulfonohydrazide and a catalytic amount (0.6 g) para-toluenesulfonic acid monohydrate. The reaction mixture was refluxed for 2 h, then cooled to room temperature. The cooled solution was filtered and the white precipitate collected by filtration. The solids were dried in vacuo; 12.8 g (yield: 67.4%) of material were collected in this fashion. The title compound was analysed by means of $^1$H-NMR spectroscopy.

Synthesis of 3,5-dimethyl-6-hydrocyclopenta[1,2-b] thiophene

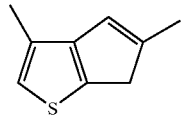

To a flask containing 11.1 g (33.3 mmol) 2-sulfonohydrazide-3,5-dimethyl-4hydrocyclopenta[1,2-b] thiophene dissolved in 50 ml THF was added a solution containing 2.5 M n-butyliithium (96 mmol, 38.4 ml) in hexane. Stirring was continued for 18 h then the reaction was quenched with a solution containing 18 g (1 mol) water dissolved in 48 ml THF added at 0° C. An additional 100 ml water was added, then the THF was removed in vacuo. The organic fraction was collected with a 20% dichloromethane in hexane solution which was washed with water, saturated sodium bicarbonato solution, then water, dried over magnesium sulfate, then filtered. Solvents were removed on a rotoevaporator yielding 2.9 g of dark orange oil, which was used in subsequent steps without further purification. The title compound was analysed by means of ¹H-NMR spectroscopy.

Synthesis of bis(2,5-dimethylthiopentalene) dimethylsilane

To 2.9 g (20 mmol) of 3,4-dimethyl-6-hydrocyclopenta[1,2-b]thiophene dissolved in 20 ml diethylether was added a 2.5 M solution containing n-butyllithium (20 mmol, 8 ml) in hexane. Stirring continued for 2 h., then the solvents were removed in vacuo. The dried solids were washed with pentane, then dissolved in 10 ml THF. In a separate flask, a solution containing 1.2 g (10 mmol) dichlorodimethylsilane and the THF solution containing the anion was added dropwise. Stirring continued for 18 h., then the solvents were removed in vacuo. The solids were washed with pentane, then pentane was removed in vacuo yielding 3.0 g of a tan free flowing powder. The title compound was analysed by means of ¹H-NMR spectroscopy.

Synthesis of dimethylsilandiylbis(3,5-dimethylthiopentalene)zirconium dichloride A 250 ml flask was charged with 3.0 g (8.41 mmol) bis(3,5-dimethylcyclopenta[1,2-b]thiophene)dimethylsilane dissolved in 60 ml diethylether. Dropwise at room temperature, a solution containing 2.5 M butyllithium in hexane (16.8 mmol, 7 ml) was added. The solution was stirred for 1.5 h. then the solvents were removed in vacuo. The solids were washed with pentane, and the dianion was obtained as a light brown powder. The title compound was analysed by means of ¹H-NMR spectroscopy.

The dianion (prepared above) was slurried in pentane (70 ml) then zirconium tetrachloride 1.96 g, 8.41 mmol) was slowly added as a dry powder. After addition was complete, a few drops of THF was added, then the slurry was stirred 18 h. Solvents were removed in vacuo, then 4.5 g of a bright yellow solid were recovered. A 3.5 g portion of this material was purified by filtering from dichloromethane and the solvents again removed in vacuo yielding 1.3 g of a 50/50 rac meso mixture; calculated yield 1.68 g (38.8%). Crystals of the rac isomer were obtained by slow evaporation of a dichloromethane solution of the rac/meso mixture. The title compound was analysed by means of ¹H-NMR spectroscopy.

EXAMPLE 4

(Comparison)

Dimethylsilandiylbis-4-(2,5-dimethyl-1-phenylcyclopentadienyl-[2,1-b]-pyrrol)zirconium dichloride-SiMe₂(Me₂PhCpPyrrol)ZrC₂

This compound was prepared according to the procedure of Example 13 described in WO 98/22486.

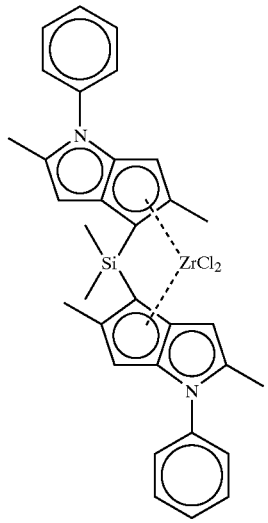

EXAMPLE 5

(Comparison)

Synthesis of dimethylsilandiylbis-4-(3-methyl-1-phenylcyclopentadienyl-[2,1-b]-pyrrol) zirconium dichloride-SiMe₂(MePhCpPyrrol)ZrCl₂

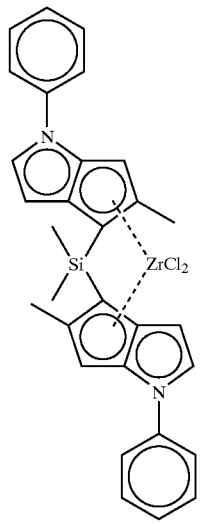

Synthesis of 1-Phenylpyrrole-2-carbaldehyde

POCl₃ (0.70 mol, 65.3 ml) was added dropwise to 76 ml of DMF and stirred for 10 min. The temperature was lowered to 0° C. and a solution of 1-phenylpyrrole (0.70 mol, 100 g) in dichloromethane (100 ml) was added dropwise. The viscous solution was slowly warmed to 50° C. and stirred for 1 h. After cooling to room temperature, the flask was opened to the air and charged with 750 g of crushed ice. A 20 wt % solution of NaOH (885 ml) was added cautiously and the mixture was immediately heated to 90–95° C. and stirred for 10 min. The flask was placed in an ice bath and the product solidified upon cooling. The solids were collected on a filter funnel, washed with water, re-dissolved in dichloromethane, and dried over MgSO₄. Evaporation of the solvent yielded 114 g of an orange oil (95% yield). ¹H-NMR showed the crude product contained ca. 10% 1-phenylpyrrole-3-carbaldehyde. The product was used without further purification. The title compound was analysed by $^1$H-NMR spectroscopy.

Synthesis of Ethyl[2Z]-2-methyl-3-[1-phenylpyrrol-2-yl]prop-2-enoate

Triethyl 2-phosphonopropionate (0.714 mol, 153 ml) was dissolved in THF (75 ml) and added slowly to NaH (1.0 mol, 24.3 g) in THF (60 ml) at 0° C. The mixture was slowly warmed to room temperature and stirring was continued for 1 h after gas evolution had ceased. The temperature was lowered to −10° C. and a solution of the above described 1-Phenylpyrrole-2-carbaldehyde (0.665 mol, 113.0 g) in 200 ml of THF was added dropwise. The flask and contents were warmed to room temperature over a 30 minute period resulting in a thick precipitate which decoupled the magnetic stirrer. A saturated solution of $NH_4Cl$ (100 ml) was added cautiously dissolving the precipitate to give a two phase solution. After evaporating the THF, the crude product was extracted with ether (2×200 ml). The extract was washed with brine solution, dried over $MgSO_4$, and solvents were removed on a rotoevaporator. Yield: 178 g of product as a white solid (98%). The title compound was analysed by $^1$H-NMR and $^{13}$C-NMR spectroscopy.

Synthesis of Ethyl 2-methyl-3-[1-phenylpyrrol-2-yl]propanoate

The hydrogenation was run in ~50 g batches as follows: A solution of the above described Ethyl[2Z]-2-methyl-3-[1-phenylpyrrol-2-yl]prop-2-enoate (0.22 mol, 55 g) in dichloromethane (300 ml) was stirred under 80 psig of hydrogen pressure at room temperature with 2.3 g of 10% Pd on carbon for 4 h. Evaporation of the filtered solution gave 54 g of the product (95% pure by GC). The title compound was analysed by $^1$H-NMR, $^{13}$C-NMR and ms spectroscopy.

Synthesis of 2-methyl-3-[1-phenylpyrrol-2-yl]propanoic acid

A mixture of ethyl 2-methyl-3-[1-phenylpyrrol-2-yl]propanoate (0.164 mol, 42.1 g) and Claisen's reagent (78 ml) were heated at 90–95° C. for 1 h. After cooling to room temperature, the solution was diluted with 75 g of crushed ice and acidified to pH 1-2 with 6 N HCl. The brown oily precipitate was dissolved in ether, washed with brine solution, dried over $MgSO_4$, and evaporated to an orange oil (21.65 g). The title compound was analysed by $^1$H-NMR spectroscopy.

Synthesis of 5-methyl-1-phenyl-5,6-dihydrocyclopenta[1,2-b]pyrrol-4-one

A solution of 2-methyl-3-[1-phenylpyrrol-2-yl]propanoic acid (0.188 mol, 43 g) in dichloroethane (75 ml) was added slowly to 1000 g of 87% PPA at 100–110° C. and stirred for 5 h. The mixture was poured onto crushed ice. A 30% (v/v) mixture of dichloromethane in hexane (200 ml) was added to dissolve the organic material. The aqueous phase was separated and re-extracted with 30% (v/v) dichloromethane in hexane (200 ml). The combined organic fractions were washed with an aqueous saturated $Na_2CO_3$ solution and dried over $MgSO_4$. After filtration, solvents were removed on a rotoevaporator yielding 37 g of product as a tan powder. The title compound was analysed by $^1$H-NMR, $^{13}$C-NMR and ms spectroscopy.

Synthesis of Hydrazone of 5-methyl-1-phenyl-5,6-dihydrocyclopenta[1,2-b]pyrrol-4-one The ketone 5-methyl-1-phenyl-5,6-dihydrocyclopenta[1,2-b]pyrrol-4-one (0.171 mol, 36 g), p-toluenesulfonhydrazide (0.177 mol, 33 g), and p-toluenesulfonic acid monohydrate (0.035 mol, 6.6 g) were stirred in 220 ml of absolute ethanol at 70° C. for 16 h. After cooling to room temperature and standing for several hours, the precipitated product was collected on a filter funnel, washed with ether, and dried under vacuum (38.5 g). Solvents were removed from the filtrate and an additional 20.4 g of product were obtained by triteration with toluene. Total yield: 58.9 g (91%). The title compound was analysed by $^1$H-NMR, $^{13}$C-NMR and ms spectroscopy.

Synthesis of 5-methyl-1-phenyl-1-azapentalene

The hydrazone of 5-methyl-1-phenyl-5,6-dihydrocyclopenta[1,2-b]pyrrol-4-one (0.086 mol, 32.5 g) was slurried in 200 ml of THF, cooled to −78° C., and treated with 2.2 eqivalents of butyllithium (0.189 mol, 76 ml of a 2.5 M solution in hexanes). The mixture was slowly warmed to room temperature and stirred for 16 h. At room temperature a saturated aqueous solution of $NH_4Cl$ was added slowly (10 ml) followed by 20 ml of water. THF was evaporated from the mixture and the residue was partitioned with ether/water. The organic fraction was dried over $MgSO_4$, filtered, and evaporated to a dark oil. The oil was extracted with hexane. Evaporation of the extract yielded 12 g of orange oil (72% yield). The title compound was analysed by $^1$H-NMR spectroscopy.

Synthesis of $Me_2(5-Me-1-Ph-4-CpPy)_2Si$

A solution of 5-methyl-1-phenyl-1-azapentalene (24 mmol, 4.7 g) in ether (60 ml) was treated with butyllithium (28 mmol, 11.2 ml of a 2.5 M solution in hexanes) and stirred for 16 h. Pentane (50 ml) was added and the slurry was filtered through a closed frit. The tan solids were re-dissolved in THF (50 ml), cooled to −78° C., and treated with a solution of $Me_2SiCl_2$ (6.7 g) in THF (50 ml). The dark brown solution was slowly warmed to 50° C. and stirred for 16 h. Volatiles were removed in vacuo and the residue was extracted with dichloromethane. Evaporation of the solvent gave 8.5 g of product as a white solid (81% yield). The title compound was analysed by $^1$H-NMR spectroscopy.

Synthesis of $Me_2Si(5-Me-1-Ph-4-CpPy)_2ZrCl_2$

A solution of $Me_2(5-Me-1-Ph-4-CpPy)_2Si$ (9.0 mmol, 4.0 g) in ether (100 ml) was cooled to −78° C., treated with butyllithium (20 mmol, 8.0 ml of a 2.5 M solution in hexanes), and warmed to room temperature. After stirring overnight, the pressure was reduced to evaporate the solvents. The residue was washed with pentane (40 ml) and dried in vacuo to a free flowing tan powder. Zirconium tetrachloride (9.0 mmol, 2.09 g) was added to the flask and the contents were stirred overnight in a mixture of pentane (75 ml) and ether (1.5 ml). The orange solids were collected on a closed frit, washed with pentane, and dried under vacuum (yield: 5.9 g). A portion of the crude product (5.65 g) was stirred in dichloromethane (75 ml) and filtered. The filtrate was concentrated to a small volume and pentane was added to precipitate the complex (yield—4.1 g of an orange powder, 50/50 rac/meso isomers). The title compound was analysed by $^1$H-NMR and $^{13}$C-NMR spectroscopy.

Propylene Polymerizations

EXAMPLE 6 TO 14

The polymerizations were conducted in a 41 stainless reactor equipped with an air-driven magnetic stirrer and steam/water temperature controlled jacket. The autoclave was swept with dry argon at 90–100° C. for 1 h prior to polymerization. The zirconocene was dissolved in 10 ml of the MAO solution, and charging to the reactor cooled to 15° C. Propene (2.2 1) was added, stirring was initiated (500 rpm), and the reactor contents were heated to the polymerization reaction within 7 minutes. After 1 h, carbon monoxide gas was charged to the reactor to terminate the run and residual monomer was vented. The reactor was cooled to room temperature, and swept with a stream of argon for several minutes before opening. The polymer was removed and dried in a vacuum oven at 80° C. for 1 h before weighing. Yield—254 g of polymer (19.9 wt % ethene by IR analysis).

TABLE 1

Bulk propene polymerization results[a]

| Ex. | Zirconocene (mg) | $T_p$, °C. | $H_2$,[f] mmol | Yield, g | Activity, Kg/g-cat/h | $T_m$, °C. | IV, dL/g | $P_{2,1}$, Mol % | mrrm, mol % |
|---|---|---|---|---|---|---|---|---|---|
| 6 | Tp[b] (0.20) | 50 | 0 | 212 | 1060 | 160 | 3.9 | n.d. | n.d. |
| 7 | Tp[b] (0.05) | 50 | 55 | 399 | 7,980 | 157 | 2.7 | n.d. | n.d. |
| 8 | Tp[b] (0.05) | 70 | 0 | 146 | 2,920 | 156 | 3.0 | 0.54 | 0.40 |
| 9 | Tp[b] (0.05) | 70 | 55 | 513 | 10,260 | 155 | 2.2 | n.d. | n.d. |
| 10 | Tp[c] (0.20) | 50 | 0 | 46 | 230 | 159 | 5.3 | n.d. | n.d. |
| 11 | Tp[c] (0.20) | 50 | 55 | 418 | 2,090 | 160 | 3.3 | n.d. | n.d. |
| 12 | Tp[c] (0.20) | 70 | 0 | 144 | 720 | 160 | 3.3 | 0.21 | 0.37 |
| 13 | Tp[c] (0.10) | 70 | 55 | 522 | 5,220 | 159 | 1.7 | n.d. | n.d. |
| 14 | Tp[d] (0.40) | 50 | 0 | 100 | 250 | 149 | 1.93 | n.d | n.d. |
| 15 (comp) | N1 (0.40) | 50 | 0 | 35 | 88 | 155 | 1.7 | n.d. | n.d. |
| 16 (comp) | N1 (0.40) | 70 | 0 | 102 | 255 | 152 | 1.0 | 0.09 | 1.43 |
| 17 (comp) | N2 (0.40) | 50 | 0 | 146 | 730 | 146 | 1.26 | n.d. | 2.1 |

[a] 2.2 L of propene, 10 mL of 10 wt % MAO in toluene, 1 h polymerization time.
[b] rac isomer
[c] 80/20 rac/meso mixture
[d] mmol of hydrogen added to the reactor.
n.d. not determined
Tp[b]: $SiMe_2(Me_2PhCpThiophen)ZrCl_2$
Tp[c]: $SiMe_2[Me_2(MePh)CpThiophen]ZrCl_2$
Tp[d]: $SiMe_2(Me_2CpThiophen)ZrCl_2$
N1: 50/50 rac/meso-$SiMe_2(Me_2PhCpPyrrol)ZrCl_2$
N2: 50/50 rac/meso-$SiMe_2(MePhCpPyrrol)ZrCl_2$.

oxide gas was charged to the reactor to terminate the run and then the residual monomer was vented. The reactor was cooled to room temperature and devolatilized with argon. The polymer was removed and dried in a vacuum oven at 50° C. for 1 h before weighing. The characterizing data of the obtained polymer is indicated in Table 1.

EXAMPLES 15 TO 17
(Comparison)

The same polymerization as described above was carried out, using metallocenes as shown in Table 1. The characterizing data of the obtained polymer is indicated in Table 1.
Ethylene-Propylene Polymerization

EXAMPLE 18

The polymerization was conducted in a 4 L stainless steel reactor equipped with an air-driven magnetic stirrer and steam/water temperature controlled jacket. The autoclave was swept with dry argon at 90° C. for 1 h prior to polymerization. $SiMe_2(Me_2PhCpThiophen)ZrCl_2$ (0.05 mg) was dissolved in a 10 wt % solution of MAO in toluene (10 mL), shaken for 10 minutes, and transferred to a stainless steel sample bomb attached to the reactor. Propene (2.2 L) was added to the cooled reactor (20° C.) and stirring was initiated (500 rpm). The catalyst solution was charged to the reactor with ethene to 100 psig overpressure of ethylene in the reactor. The reactor and contents were heated to 50° C. within 5–7 minutes and the ethene feed was adjusted to maintain 100 psig overpressure above the vapor pressure of propene. After 1 h, carbon monoxide gas was charged to the reactor to terminate the run and residual monomer was vented. The reactor was cooled to room temperature, and swept with a stream of argon for several minutes before opening. The polymer was removed and dried in a vacuum

What is claimed is:
1. A metallocene compound of the general formula (I):

(I)

wherein
Y is a moiety of formula (II)

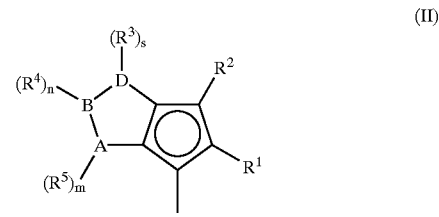

(II)

wherein
A, B and D, same or different from each other, are selected from an element of the groups 14 to 16 of the Periodic Table of the Elements (new IUPAC version), with the exclusion of nitrogen and oxygen; $R^1$, $R^2$, $R^3$, $R^4$ and $R^5$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms; wherein two $R^3$ can form a ring comprising 4 to 8 atoms, and $R^3$ and $R^4$ can form a ring comprising 4 to 8 atoms, which can bear substituents; with the proviso that when s is 0 or when $R^3$ is hydrogen, $R^2$ is not hydrogen;

n, m and s are selected from 0, 1 and 2;

n, m and s being 0 when A, B and D are selected from an element of the group 16 of the Periodic Table of the Elements (new IUPAC version);

n, m and s being 1 when A, B and D are selected from an element of the group 15 of the Periodic Table of the Elements (new IUPAC version);

n, m and s being 1 or 2 when A, B and D are selected from an element of the group 14 of the Periodic Table of the Elements (new IUPAC version);

and wherein the ring containing A, B and D can have double bonds in any of the allowed positions;

Z is selected from a moiety of formula (II) as described above and from a moiety of formula (III):

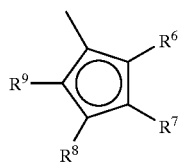
(III)

wherein $R^6$, $R^7$, $R^8$ and $R^9$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms, $R^7$ being different from hydrogen; optionally $R^6$ and $R^7$ can form a ring comprising 4 to 8 carbon atoms, which can bear substituents;

and when Z is a moiety of formula (II), Y and Z can be the same or different from each other;

L is a divalent bridging group;

M is an atom of a transition metal selected from those belonging to group 3, 4, 5, 6 or to the lanthanide or actinide groups in the Periodic Table of the Elements (new IUPAC version), X, same or different, is a hydrogen atom, a halogen atom, a $R^{10}$, $OR^{10}$, $OSO_2CF_3$, $OCOR^{10}$, $SR^{10}$, $NR^{10}_2$ or $PR^{10}_2$ group, wherein the substituents $R^{10}$ are defined as $R^7$;

p is an integer of from 0 to 3, being equal to the oxidation state of the metal M minus 2.

2. The metallocene compound according to claim 1, wherein the transition metal M is selected from titanium, zirconium and hafnium.

3. The metallocene compound according to claim 1, wherein X are chlorine atoms or methyl groups.

4. The metallocene according to claim 1, wherein L is =Si($R^{17}$)$_2$ or =C($R^{17}$)$_2$, wherein $R^{17}$, equal or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally two $R^{17}$ can form a cycle comprising from 3 to 8 atoms.

5. The metallocene according to claim 4, wherein L is selected from the group consisting of Si(CH$_3$)$_2$, Si(phenyl)$_2$, CH$_2$ and C(CH$_3$)$_2$.

6. The metallocene according to claim 1, wherein A is selected from sulfur, selenium, tellurium and polonium and B and D are selected from the group 14 of the Periodic Table of the Elements (new IUPAC version).

7. The metallocene according to claim 6, wherein A is sulfur and B and D are carbon atoms.

8. The metallocene compound according to claim 1, wherein Z is moiety of the formula (IV):

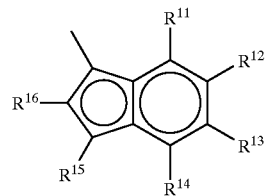
(IV)

wherein $R^{11}$, $R^{12}$, $R^{13}$, $R^{14}$, $R^{15}$ and $R^{16}$, same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms, optionally $R^{13}$ and $R^{14}$ can form a ring comprising 4 to 8 atoms which can bear substituents.

9. The metallocene compound according to claim 8, wherein $R^{14}$ is a $C_6$–$C_{20}$-aryl group and $R^{16}$ is a $C_1$–$C_{20}$-alkyl group.

10. The metallocene compound according to claim 1, wherein both Y and Z are a moiety of formula (II), A is an element of the group 16 of the Periodic Table of the Elements (new IUPAC version), B and D are carbon atoms, $R^1$ is a $C_1$–$C_{20}$-alkyl group, $R^2$ is hydrogen, $R^3$ is different from hydrogen, m is 0, n and s are 1.

11. The metallocene compound according to claim 10, wherein A is sulfur, $R^3$ is a $C_6$–$C_{20}$-aryl group or a $C_7$–$C_{20}$-alkylaryl group, the alkyl group being ortho-substituted to the aryl substituent, $R^4$ is different from hydrogen, $R^5$ is hydrogen.

12. The metallocene compound according to claim 10, wherein $R^1$ is a methyl group, $R^3$ is a phenyl group, a naphthyl group or an ortho-methylphenyl group.

13. The metallocene compound according to claim 10, being dimethylsilandiylbis-6-(2,5-dimethyl-3-phenylcyclopentadienyl-[1,2-b]-thiophene) zirconium dichloride, dimethylsilandiylbis-6-(3,5-dimethylcyclopentadienyl-[1,2-b]-thiophene) zirconium dichloride or dimethylsilandiylbis-6-[2,5-dimethyl-3-(2'-methylphenylcyclopentadienyl-[1,2-b]-thiophene] zirconium dichloride.

14. The metallocene compound according to claim 1, wherein both Y and Z are a moiety of formula (II), L is a =C($R^{17}$)$_2$ group, $R^1$ is a hydrogen atom, $R^2$ is different from hydrogen.

15. The metallocene compound according to claim 1, wherein both Y and Z are a moiety of formula (II), m is 2 and $R^5$ is not hydrogen.

16. A ligand of formula (V):

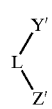
(V)

wherein Y' is a moiety of formula (VI):

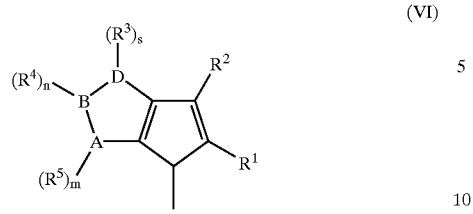

(VI)

and/or its double bond isomers;

$R^1$, $R^2$, $R^3$, $R^4$, A, B, D, n, m and s are defined as described in claim 1;

Z' is selected from a moiety of formula (VI) and from a moiety of formula (VII):

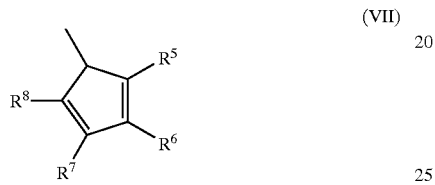

(VII)

and/or its double bond isomers;

$R^5$, $R^6$, $R^7$ and $R^8$ are defined as described in claim 1;

when Z' is equal to Y', A, B and D in Y' and Z' can be the same or different from each other;

L is a divalent bridge as defined in claim 1.

17. The ligand of formula (V) according to claim 16, wherein both Z' and Y' are a moiety of formula (VI), $R^1$ and $R^4$ are $C_1$–$C_{20}$-alkyl groups, $R^2$ is hydrogen, $R^3$ is a $C_6$–$C_{20}$-aryl or a $C_7$–$C_{20}$-alkylaryl group, A is selected from sulphur, selenium, tellurium and polonium, B and D are selected from the group 14 of the Periodic Table of the Elements (new IUPAC version), the divalent bridging group L is $(CH_3)_2Si=$, $Ph_2Si=$, $CH_2C=$ or $(CH_3)_2C=$.

18. The ligand according to claim 17, wherein A is sulfur and B and D are carbon atoms.

19. The ligand of formula (V) according to claim 16, wherein Z' is a moiety of formula (VIII):

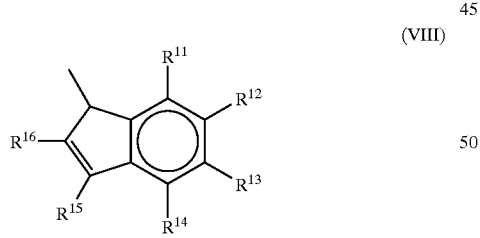

(VIII)

and/or its double bond isomers;

wherein $R^{11}$, $R^{12}$, $R^{13}$, $R^{14}$, $R^{15}$ and $R^{16}$ are defined as in claim 8.

20. The ligand according to claim 16, being dimethylbis-6-(2,5-dimethyl-3-phenylcyclopentadienyl-[1,2-b]-thiophene)silane, dimethylbis-6-(3,5-dimethylcyclopentadienyl-[1,2-b]-thiophene)silane and dimethylbis-6-[2,5-dimethyl-3-(2'-methylphenyl)cyclopentadienyl-[1,2-b]-thiophene]silane.

21. A process for the preparation of a ligand of formula (V) as defined in claim 16, D being a carbon atom and $R^2$ is a hydrogen, comprising the following step:

a) contacting a compound of general formula (IX):

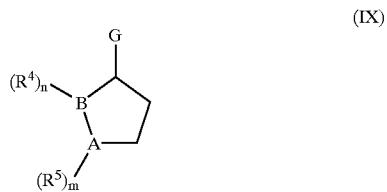

(IX)

wherein the double bonds can be in any of the allowed positions;

A, B, $R^4$, $R^5$, n and m have the meaning as defined in claim 1, G is a halogen atom, with an alkylation agent selected from $(R^3)_5MgQ$, $(R^3)_5M'$ being an alkali metal selected from sodium, potassium and lithium, or a metal selected from the group 10 to 12 from the Periodic Table of the Elements (new IUPAC version), Q being a halogen selected from chloride, bromide and iodide, in the presence of a coupling agent;

b) contacting a compound obtained under a) with a compound of general formula (X):

(X)

wherein $R^1$ has the same meaning as defined in claim 1; in the presence of a ring-closure agent, to obtain the compound of the general formula (XI):

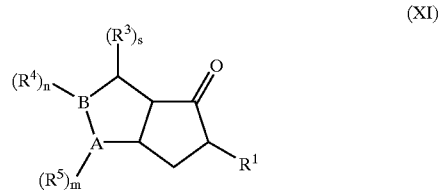

(XI)

c) conversion into the compound of formula (XII):

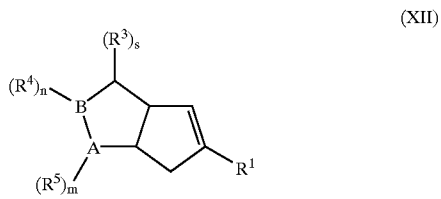

(XII)

and when Z' is equal to Y', wherein A and B in Y' and Z' are the same or different from each other:

d1) treating the compound of formula (XII) with a base selected from hydroxides and hydrides of alkali- and earth-alkali metals, metallic sodium and potassium, and organometallic lithium salts, and subsequent contacting with a compound of formula $LQ_2$ (XIII), wherein L has the same meaning as defined in claim 1, and Q is a halogen, wherein the molar ratio between the compound of formulae (XII) and (XIII) is at least 2;

or when Z' is a compound of formula (VII):
- d2) treating the compound of formula (XII) with a base as defined under d1), and subsequently contacting with a compound of formula Z'LQ (XIV), wherein L has the same meaning as defined in claim 1, and Q is a halogen;

or
- where Y' is equal to Z' and $R^2$ is defined as $R^7$:
  - treating the ligand of formula (V) with a base as defined under d1), wherein the molar ratio between the base and the compound of formuls (V) is at least 2, and subsequent with a compound of formula $R^2Q$, Q being a halogen atom selected from chloride, iodeide and bromide.

22. The process according to claim 21, wherein the ring-closing agent is selected from phosphorus pentoxide-methansulfonic acid (PPMA) and polyphosphoric acid (PPA).

23. The process according to claim 21, wherein the compound of general formula (X) is methacrylic acid.

24. The process according to claim 21, wherein the compound of general formula (IX) is 1-methyl-3-phenyl-thiophene.

25. The process according to claim 21, wherein the conversion into the compound of formula (XII) is carried out in the presence of a reduction agent and para-toulene sulfonic acid monohydrate.

26. The process according to claim 21, wherein the reduction agent is lithium aluminium hydride ($LiAlH_4$).

27. The process according to claim 21, wherein G is a bromine atom.

28. The process according to claim 21, wherein the compound of formula $LQ_2$ (XIII) is dimethyldichlorsilane.

29. The process according to claim 21, wherein the base is butyllithium.

30. The process according to claim 21, wherein the coupling agent used in step 1 is a Ni, Pd or Pt-based coupling agent.

31. The process according to claim 30, wherein the coupling agent is bis(diphenylphosphino)propane)] dichloronickel(II) (Ni(dPPP)).

32. A process for the preparation of a metallocene compound according to claim 1, obtainable by contacting the ligand of formula (V) according to claim 16, with a compound capable of forming a corresponding dianionic compound thereof and thereafter with a compound of formula $MX_{p+2}$, wherein M, X and p are defined as in claim 1.

33. The process according to claim 32, wherein the compound able to form said corresponding dianionic compound is selected from the group consisting of hydroxides and hydrides of alkali- and earth-alkali metals, metallic sodium and potassium, and organometallic lithium salts.

34. The process according to claim 33, wherein the compound able to form said dianionic compound is n-butyllithium.

35. The process according to claim 32, wherein the compound of formula $MX_{p+2}$ is selected from titaniumtetrachlorid, zirconiumtetrachlorid and hafniumtetrachlorid.

* * * * *